United States Patent
Bilton et al.

(10) Patent No.: US 10,322,242 B2
(45) Date of Patent: Jun. 18, 2019

(54) MECHANISM FOR A DRUG DELIVERY DEVICE AND DRUG DELIVERY DEVICE COMPRISING THE MECHANISM

(71) Applicant: Sanofi, Paris (FR)

(72) Inventors: Simon Lewis Bilton, Warwickshire (GB); Michael Bainton, Kineton (GB); William Marsh, Buckingham (GB); Matthew Jones, Warwick (GB)

(73) Assignee: Sanofi, Paris (FR)

( * ) Notice: Subject to any disclaimer, the term of this patent is extended or adjusted under 35 U.S.C. 154(b) by 262 days.

(21) Appl. No.: 14/916,070

(22) PCT Filed: Sep. 3, 2014

(86) PCT No.: PCT/EP2014/068647
§ 371 (c)(1),
(2) Date: May 27, 2016

(87) PCT Pub. No.: WO2015/032774
PCT Pub. Date: Mar. 12, 2015

(65) Prior Publication Data
US 2016/0206827 A1    Jul. 21, 2016

(30) Foreign Application Priority Data
Sep. 3, 2013 (EP) .................................. 13182751

(51) Int. Cl.
*A61M 5/31* (2006.01)
*A61M 5/315* (2006.01)

(52) U.S. Cl.
CPC .......... *A61M 5/31551* (2013.01); *A61M 5/31* (2013.01); *A61M 5/31548* (2013.01); *A61M 5/31586* (2013.01); *A61M 2005/3126* (2013.01)

(58) Field of Classification Search
CPC ...... A61M 2005/3126; A61M 5/31551; A61M 5/31583; A61M 5/31541; A61M 5/31528;
(Continued)

(56) References Cited

U.S. PATENT DOCUMENTS 5,961,495 A * 10/1999 Walters ............. A61M 5/31553
604/111
2010/0168677 A1 * 7/2010 Gabriel ............. A61M 5/31551
604/189
(Continued)

FOREIGN PATENT DOCUMENTS

| EP | 1819382 | 10/2009 |
|---|---|---|
| WO | WO99/38554 | 8/1999 |
| WO | WO2010/020311 | 2/2010 |
| WO | WO2012/037939 | 3/2012 |

OTHER PUBLICATIONS

International Search Report and Written Opinion in International Application No. PCT/EP2014/068647, dated Nov. 19, 2014, 10 pages.
(Continued)

*Primary Examiner* — Lauren P Farrar
(74) *Attorney, Agent, or Firm* — Fish & Richardson P.C.

(57) ABSTRACT

The mechanism includes a body defining an axial direction, a dial that is moved for setting a dose, an indicator member coupled with the dial, and a movable window displaying a surface area of the indicator member. The indicator member is axially moved relative to the body.

18 Claims, 18 Drawing Sheets

(58) Field of Classification Search
CPC .......... A61M 5/31543; A61M 5/31593; A61M 5/3155; A61M 5/31525
USPC ................................ 604/207–209, 211, 228
See application file for complete search history.

(56) References Cited

U.S. PATENT DOCUMENTS

| | | | |
|---|---|---|---|
| 2010/0274198 A1* | 10/2010 | Bechtold ........... | A61M 5/31551 604/189 |
| 2014/0200519 A1* | 7/2014 | Kjeldsen ............ | A61M 5/3129 604/207 |
| 2015/0367077 A1* | 12/2015 | Plambech ........... | A61M 5/1452 604/111 |
| 2016/0045664 A1* | 2/2016 | Morris .............. | A61M 5/31551 604/207 |
| 2016/0058950 A1* | 3/2016 | Marsh ..................... | A61M 5/20 604/211 |
| 2016/0067408 A1* | 3/2016 | Morris .............. | A61M 5/31528 604/208 |

OTHER PUBLICATIONS

International Preliminary Report on Patentability in International Application No. PCT/EP2014/068647, dated Mar. 8, 2016, 8 pages.
Rote Liste, "50. Hypophysen-, Hypothalamushormone, andere regulatorische Peptide u. ihre Hemmstoffe," Chapter 50, ed. 2008, 20 pages.

* cited by examiner

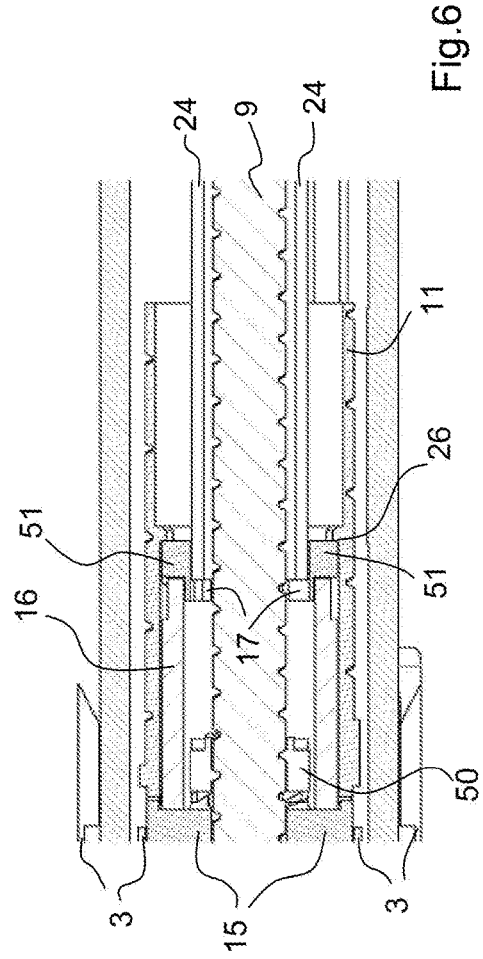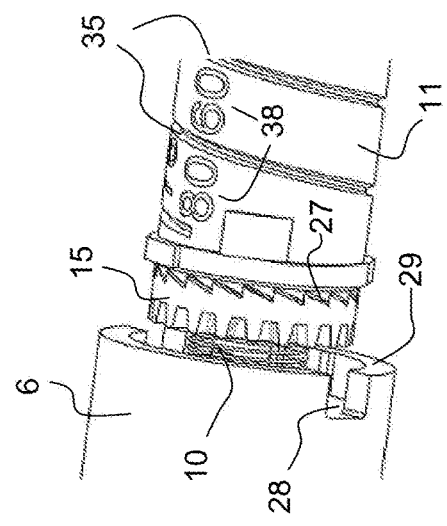

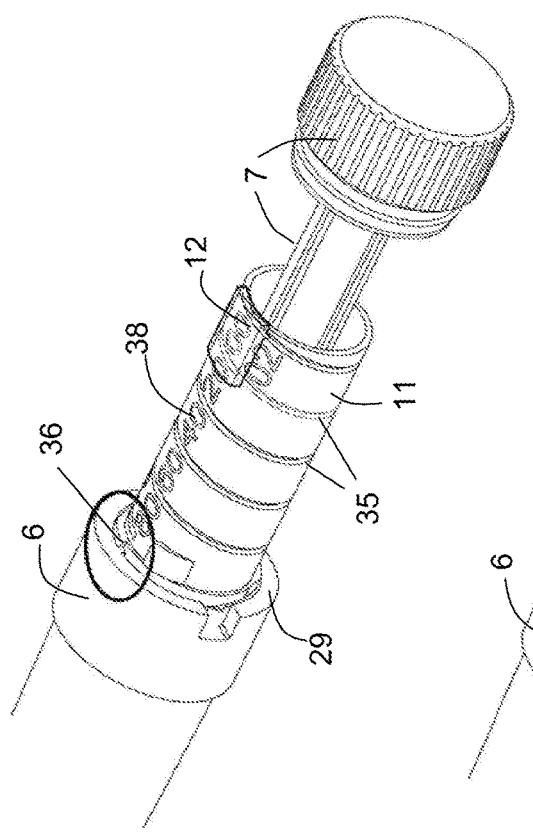

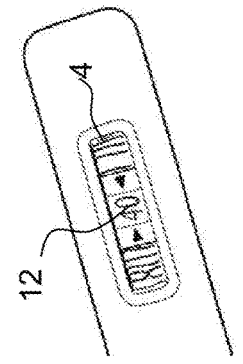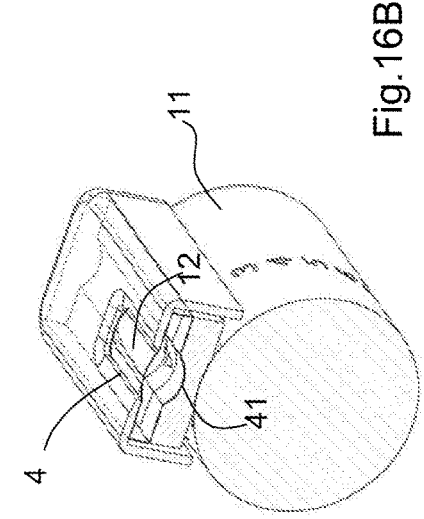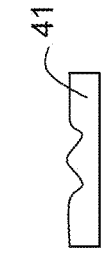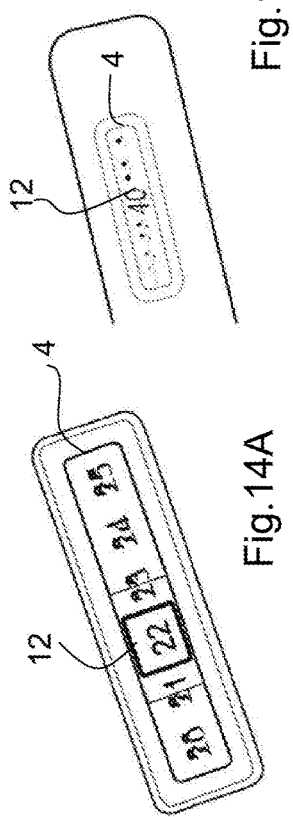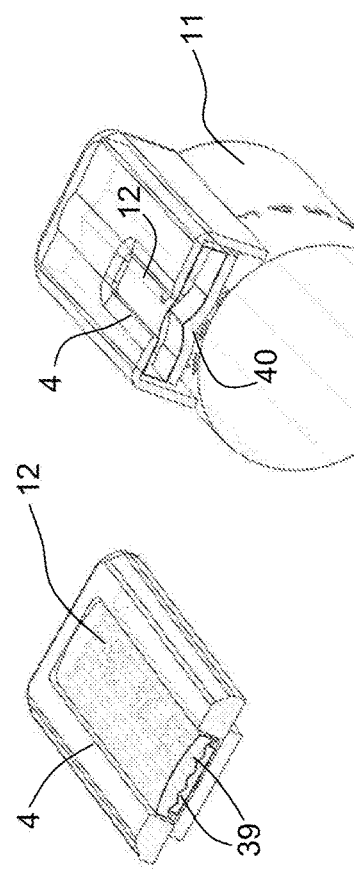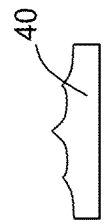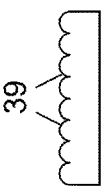
Fig.14A Fig.15A Fig.16A
Fig.14B Fig.15B Fig.16B
Fig.14C Fig.15C Fig.16C

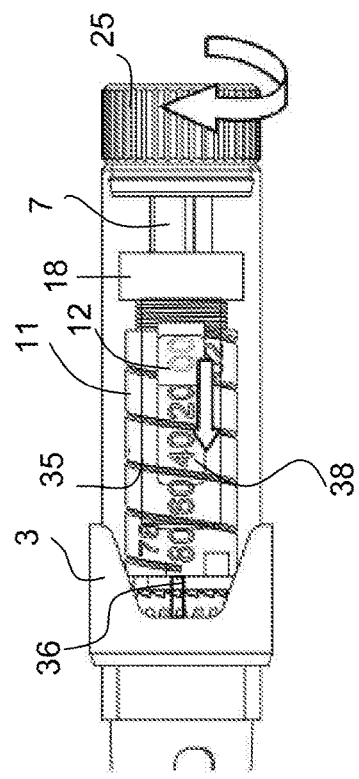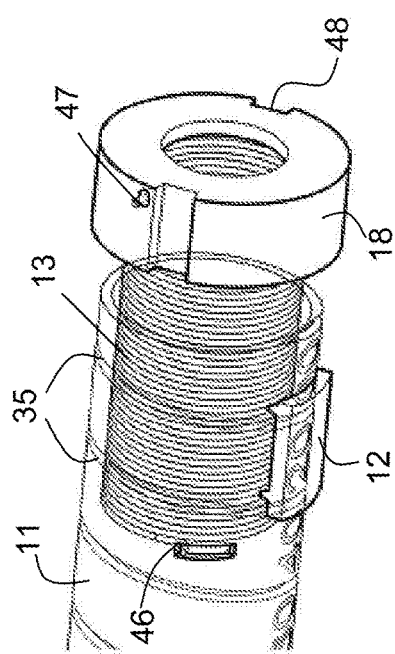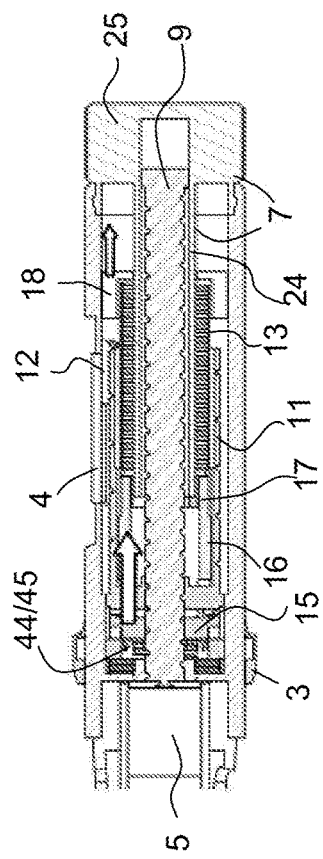

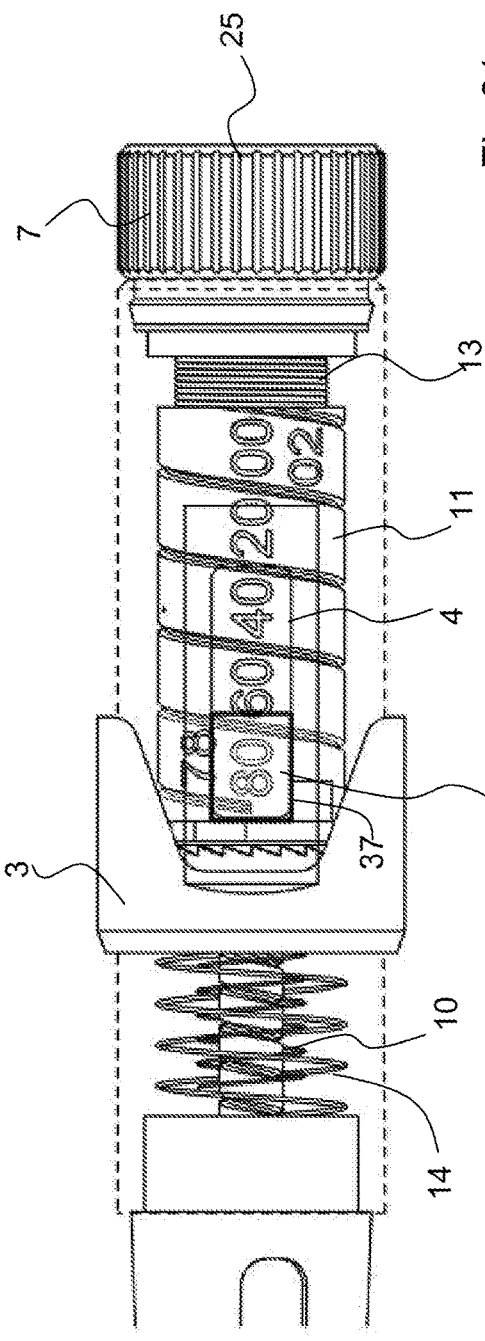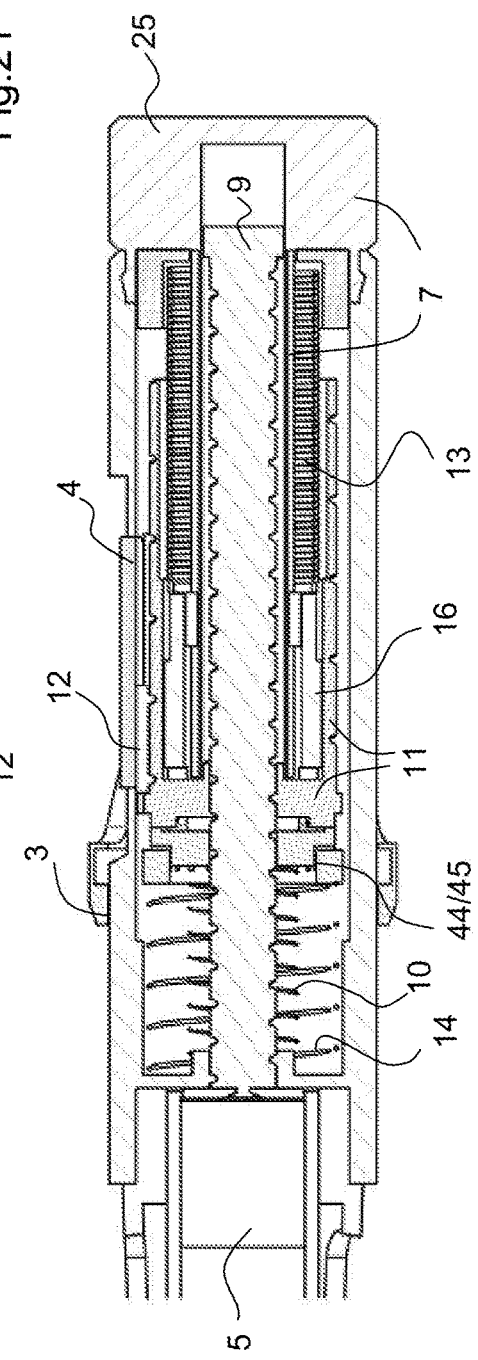

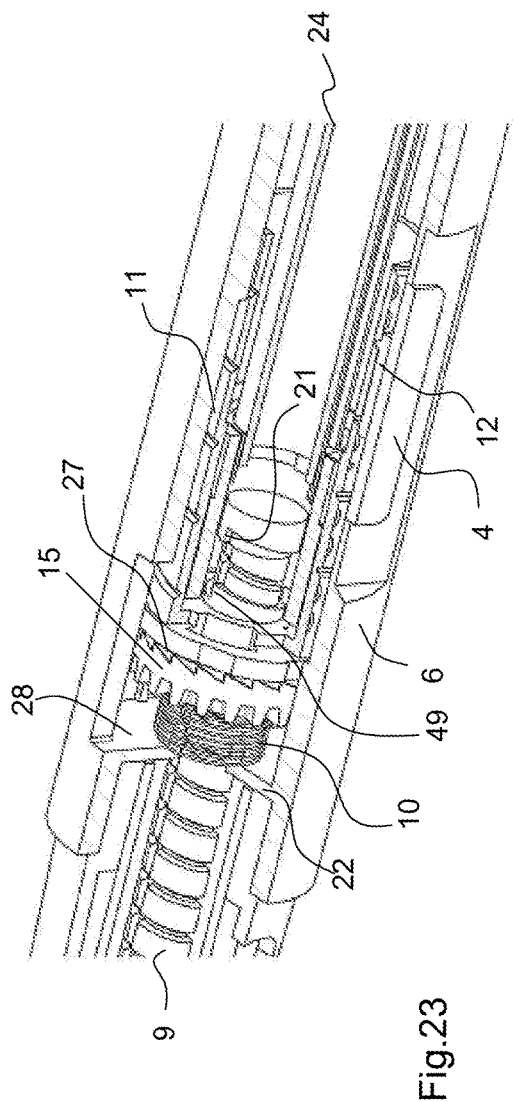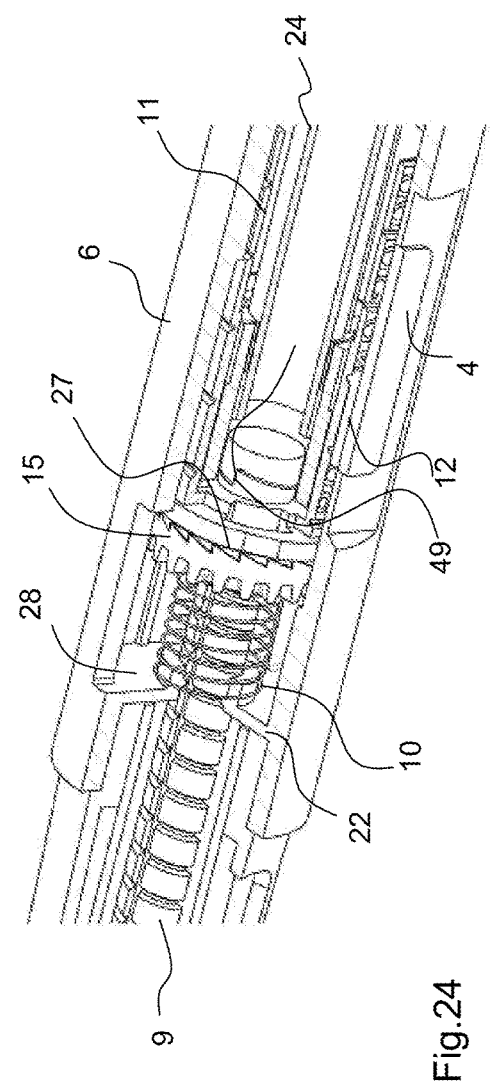

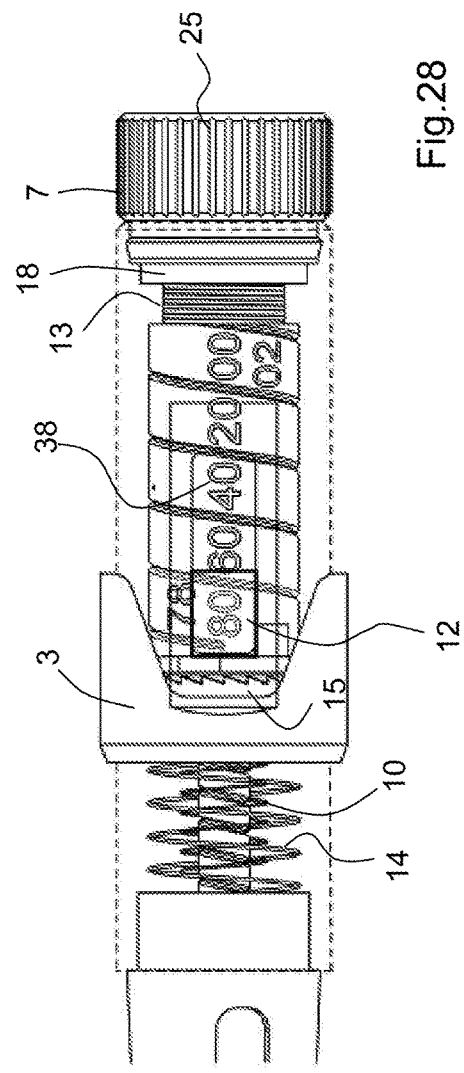
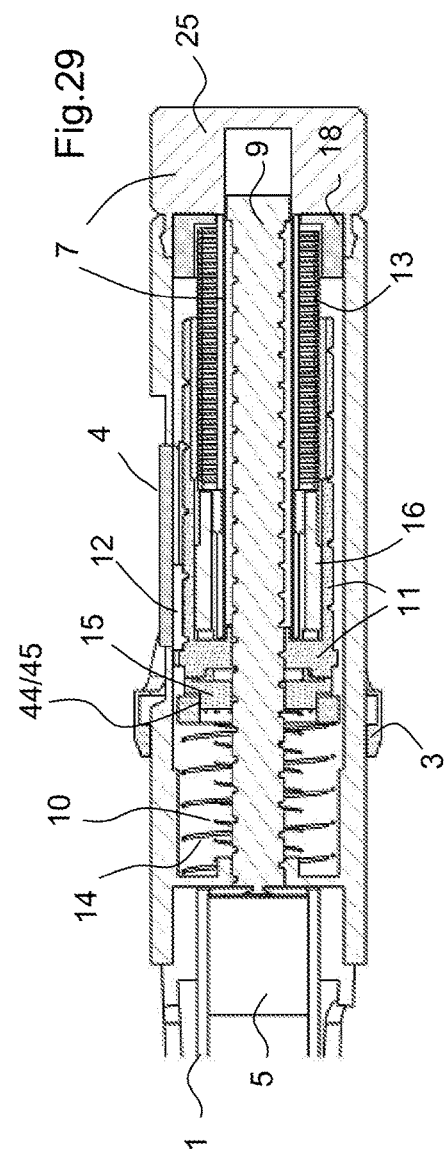

MECHANISM FOR A DRUG DELIVERY DEVICE AND DRUG DELIVERY DEVICE COMPRISING THE MECHANISM

CROSS-REFERENCE TO RELATED APPLICATIONS

This application is a U.S. national stage application under 35 USC § 371 of International Application No. PCT/EP2014/068647, filed on Sep. 3, 2014, which claims priority to European Patent Application No. 13182751.1, filed on Sep. 3, 2013, the entire contents of which are incorporated herein by reference.

TECHNICAL FIELD

This disclosure relates to a mechanism for use in a drug delivery device that can be operated to deliver a number of user variable doses of medicament.

BACKGROUND

EP 1 819 382 B1 describes an injection device comprising a housing, a dose setting member, a torsion spring connected to the dose setting member in such a way that energy is accumulated in the torsion spring upon rotation of the dose setting member, and a rotatably mounted display member, which is threadedly engaged with the housing, coupled with the dose setting member and provided to display the dose set. A drive member is coupled with the dose setting member via a unidirectional ratchet. Upon release of a locking member, the torsion spring rotates the drive member, and the drive member rotates a piston rod, which is helically advanced by a threaded engagement with the housing. The dose setting member is axially retractable, and the dose set can be reset or reduced when the dose setting member is pulled to disengage the ratchet.

WO 2010/020311 A1 describes an injection device comprising a housing with a first window provided with a first lens, and an inner sleeve with a second window provided with a second lens, which slides axially within the first window to display numbers indicating the size of a selected dose. The numbers are helically arranged on an axially locked rotatable dial sleeve, which is arranged inside the inner sleeve and is threadedly engaged with the inner sleeve. The rotation of the dial sleeve is synchronized with the displacement of the second window. The lens in the first window distorts the display, and the lens in the second window compensates for the distortion to increase the legibility of the number viewed through both windows.

SUMMARY

In some aspects of the present invention, a new mechanism for a drug delivery device facilitates the use of the drug delivery device. In certain aspects, a new drug delivery device facilitates the use of the drug delivery device.

In one aspect the invention relates to a mechanism for a drug delivery device. The mechanism comprises a body defining an axial direction, a dial that is moved for setting a dose by a user, an indicator member, which may be used to indicate the amount of a dose of a drug, coupled with the dial, and a movable window displaying a surface area of the indicator member. The indicator member is axially moved relative to the body.

The movable window allows a surface area of the indicator member to be selected for display.

In an embodiment the mechanism further comprises a window arrangement comprising the movable window that is coupled to the indicator member.

Coupling the movable window to the indicator member allows to select the displayed area according to a movement of the indicator member.

In a further embodiment the mechanism further comprises a fixed window in the body, the fixed window and the movable window forming the window arrangement, the movable window being axially movable within dimensions of the fixed window, particularly within an area that is occupied by the fixed window, and displaying a surface area of the indicator member.

The fixed window defines an area of the body where the display is provided, while the movable window selects the portion of the indications on the indicator member that is to be displayed.

In a further embodiment of the mechanism the fixed window comprises features for optical distortion, and the movable window provides a correction of the optical distortion. The optical distortion may be provided to render the indication illegible, for instance.

The optical distortion allows an area of the indication to be selected for display while another area is rendered illegible by the distortion.

In a further embodiment of the mechanism the features for optical distortion comprise a plurality of parallel ridges, a surface of the movable window that faces the fixed window being provided with ridges correcting the distortion, and the ridges are arranged in the axial direction, allowing the movable window to move with respect to the fixed window.

The ridges provide an easy way to effect the distortion and to allow the movable window to slide in the axial direction.

In a further embodiment of the mechanism the features for optical distortion comprise a distorting lens, and the movable window has a shape correcting the distortion. The correction may be provided by a shape of the movable window that is complementary to the distorting lens and eliminates the optical effect of the lens.

The distorting lens is easily realized in a transparent material that may be used for the fixed window.

In a further embodiment of the mechanism the distorting lens has a V-shaped cross section transverse to the axial direction.

The V-shaped cross section transverse to the axial direction provides an easy way to effect the distortion and to allow the movable window to slide in the axial direction.

In a further embodiment of the mechanism the features for optical distortion comprise a magnifying lens, and the movable window has a shape compensating an optical effect of the magnifying lens.

The magnifying lens is easily realized in a transparent material that may be used for the fixed window.

In a further embodiment of the mechanism the movable window is threadedly engaged with the indicator member.

The threaded engagement allows the movable window to be moved by a movement of the indicator member, particularly to be moved in the axial direction by a helical movement of the indicator member.

In a further embodiment the mechanism further comprises a helical path of numbers on the indicator member, the helical path of numbers having a pitch that matches the pitch of the thread coupling the indicator member and the movable window.

The arrangement of the numbers allows the correct indication to be displayed in the movable window.

In a further embodiment of the mechanism an axial movement of the indicator member generates a movement of the movable window in the opposite axial direction relative to the indicator member.

The opposite movements are favourable for a reduction of the overall size of the mechanism.

In a further embodiment of the mechanism an axial movement of the indicator member generates a movement of the movable window in the opposite axial direction relative to the body.

The opposite movements are favourable for a reduction of the overall size of the mechanism.

In a further embodiment the mechanism comprises a body defining a proximal and a distal direction, a rotatable dial extending from the body in the proximal direction, a lead screw, which is threadedly engaged with the body and may be used to advance a bung in a drug cartridge, an indicator member, particularly for indicating an amount of a drug, coupled with the dial, a main spring that is loaded by a rotation of the indicator member relative to the body, a drive member rotationally locked to the lead screw, and a trigger, which rotationally locks the drive member to the body in such a way that the rotational locking can be released. The indicator member is threadedly engaged with the lead screw and with a movable window displaying a surface area of the indicator member. An intermediate sleeve is rotationally locked to the indicator member. A dial nut is rotationally locked to the dial and engages the intermediate sleeve in a unidirectional rotational gear or ratchet, thus coupling the indicator member with the dial. The drive member is unidirectionally rotationally coupled to the indicator member, and the rotational locking of the drive member to the body is released by moving the trigger in the distal direction.

The dial is used for setting and cancelling a dose of a drug and rotates the indicator member, which is coupled with the drive member via the dial nut and the intermediate sleeve in such a manner that a set dose can be cancelled by rotating the dial back. The cancellation step makes use of the unidirectional gears or ratchets. The indicator member is moved according to the threaded engagement with the lead screw, which is stationary during dose setting. The trigger is used to release energy that is stored in the main spring.

In an embodiment of the mechanism the indicator member is threadedly engaged with the lead screw in a way to allow a helical movement of the indicator member relative to the body as long as the lead screw is rotationally locked to the body via the drive member and the trigger during setting or cancelling of a dose of a drug by the user. The movable window is threadedly engaged with the indicator member in such a manner that the helical movement of the indicator member in the proximal direction generates an axial movement of the movable window in the distal direction and the helical movement of the indicator member in the distal direction generates an axial movement of the movable window in the proximal direction.

The opposite movements are favourable for a reduction of the overall size of the mechanism.

In a further embodiment the mechanism further comprises a fixed window in the body, the movable window being axially movable within dimensions of the fixed window, particularly within an area occupied by the fixed window, and displaying a surface area of the indicator member.

This allows a portion of the indications provided on the indicator member to be displayed.

In a further embodiment of the mechanism the intermediate sleeve axially contacts the drive member, so that the unidirectional rotational coupling between the indicator member and the drive member can be released by a movement of the intermediate sleeve in the distal direction. Turning the dial in one sense of rotation generates a helical movement of the indicator member in the proximal direction via the unidirectional rotational gear or ratchet, while turning the dial in the opposite sense of rotation releases the coupling between the indicator member and the drive member by means of the unidirectional rotational gear or ratchet and reverses the helical movement of the indicator member.

The unidirectional coupling allows a dose set to be cancelled by an opposite rotation of the indicator member without affecting the position of the drive member.

In a further embodiment the mechanism further comprises a resilient element between the body and the drive member, the resilient element acting on the drive member in the proximal direction. The indicator member is arranged in the proximal direction relative to the drive member, and the resilient element acts on the drive member to keep the drive member coupled to the indicator member.

The resilient element allows the coupling between the drive member and the indicator member to be removed when the dose set is cancelled.

In a further embodiment the mechanism further comprises a spline of the trigger and a spline of the drive member, the splines rotationally locking the drive member to the trigger in such a way that the rotational locking can be released. A trigger spring acts on the trigger in the proximal direction to keep the drive member rotationally locked to the trigger.

The splines provide a rotational locking that is easily engaged and disengaged. The trigger spring tends to keep the locking features engaged and is easily compressed to allow the locking features to be disengaged.

In a further embodiment of the mechanism the dial is axially constrained to the body.

Keeping the dial at the same axial position with respect to the body facilitates the operation.

In a further aspect the invention relates to a drug delivery device comprising a mechanism as recited above. In particular the drug delivery device may be a pen-type device and/or a disposable device, which is not refilled when it is empty. The drug delivery device may especially be an injection device, in particular a pen-type injector.

The term "drug", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(w-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(02)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(02)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp (O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2) 25, Asp28] Exendin-4(S1-39)-(Lys)6-NH2,
H-Asn-(Glu)5-des Pro36, Pro37, Pro38 [Met(O)14, Trp (O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The following is a detailed description of embodiments of the mechanism and drug delivery device in conjunction with the appended drawings.

BRIEF DESCRIPTION OF THE DRAWINGS

FIG. 6 shows a schematic cross section of the middle section of the embodiment according to FIG. 2.

FIG. 7 is a cutaway view of a distal part of the mechanism.

FIG. 12 is a further cutaway view of the part of the mechanism according to FIG. 7 for another state of the mechanism.

FIG. 13 is the cutaway view of FIG. 12 for still another state of the mechanism.

FIG. 14 shows an example of a display of the drug delivery device.

FIG. 15 shows a further example of the display.

FIG. 16 shows still a further example of the display.

FIG. 18 is a semitransparent view of a proximal section of an embodiment of the mechanism.

FIG. 19 is a semitransparent view of the proximal section of the embodiment according to FIG. 11 including details from FIGS. 17 and 18 for the state of the mechanism before dialling.

FIG. 20 shows a cross section of the proximal section according to FIG. 19.

FIG. 21 is a semitransparent view according to FIG. 19 for the state of the mechanism after dialling.

FIG. 22 shows a cross section according to FIG. 20 for the state of the mechanism according to FIG. 21.

FIG. 23 is a further cutaway view of the middle section of the embodiment of the mechanism including details from FIGS. 4 and 17.

FIG. 24 is a cutaway view according to FIG. 23 for the state of the mechanism after dialling the final dose.

FIG. 28 is a semitransparent view according to FIG. 21 for a state of the mechanism after setting and before dispensing a dose.

FIG. 29 is a cross section according to FIG. 22 for the state of the mechanism according to FIG. 28.

DETAILED DESCRIPTION

Figure 1:
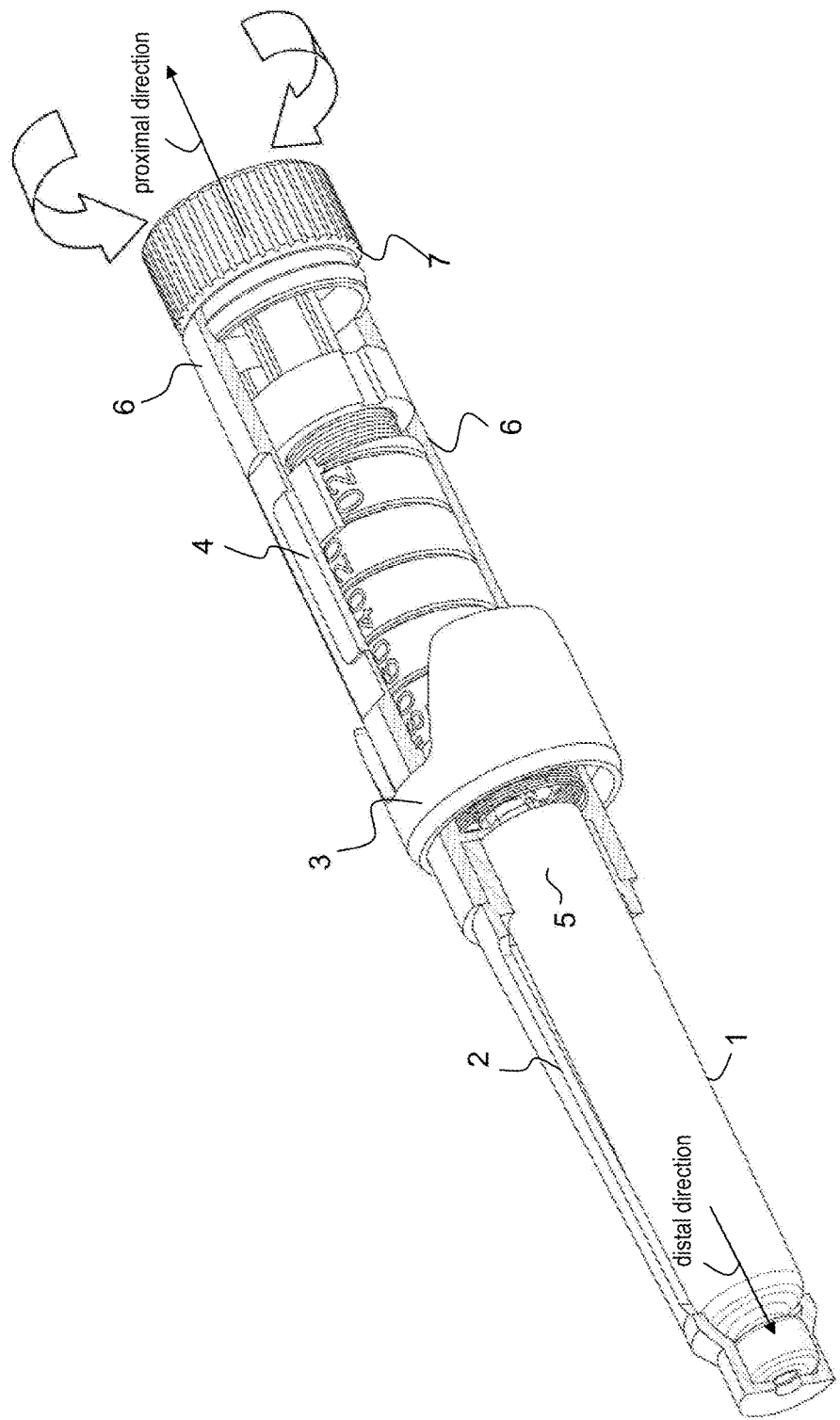
FIG. 1 is a cutaway view of a pen-type injector.

FIG. 1 is a cutaway view of a pen-type injector comprising an embodiment of the mechanism. The pen-type injector is shown as an example of the drug delivery device, and the mechanism is also suitable for other types of drug delivery devices. The pen-type drug delivery device comprises a receptacle for a drug like a medicament cartridge 1 placed in a cartridge holder 2, which may be provided to facilitate the assembling of the device. A trigger 3 is provided for the operation of the mechanism and enables the delivery of a dialled dose of the drug by means of a bung 5. A display may include a fixed window 4, which is formed in the body 6 of the device. A receptacle for the drug or a compartment for a cartridge can be formed by the body 6. If a cartridge holder 2 is used, it is fastened to the distal end of the body 6. The body 6 may be formed as a unity or may comprise an external housing and one or more inserted parts. A dial 7 is provided for the operation of the mechanism and is used to dial a dose of the drug. The rotation of the dial 7 is indicated in FIG. 1 by curved arrows. The mechanism will be described for an embodiment in which a clockwise rotation of the dial 7, as viewed in the distal direction, increases the dialled dose and a counterclockwise rotation of the dial 7 decreases the dialled dose and may particularly cancel the dose completely. In other embodiments the operation of the dial 7 may be reversed, depending on how the elements of the mechanism are coupled.

The body 6 and the entire drug delivery device comprising the body 6 have a distal end and a proximal end. The term "distal end" designates that end of the body, the device or a component thereof which is or is to be arranged closest to a dispensing end of the drug delivery device. The term "proximal end" designates that end of the body, the device or a component thereof which is or is to be arranged furthest away from the dispensing end of the drug delivery device. The term "distal direction" means the direction from the proximal end towards the distal end. The term "proximal direction" means the direction from the distal end towards the proximal end. In FIG. 1 these directions are indicated by straight arrows, which also indicate the axial directions with respect to the body 6 and furthermore define an axis of the body 6. The terms "axial movement" and "translation" will be used to describe a movement of an element of the mechanism relative to the body 6 in the axial direction, and this movement may or may not include a rotation around the axis. The terms "rotation" and "rotational" will be used to describe a movement of an element of the mechanism relative to the body 6 around the axis.

Figure 2:
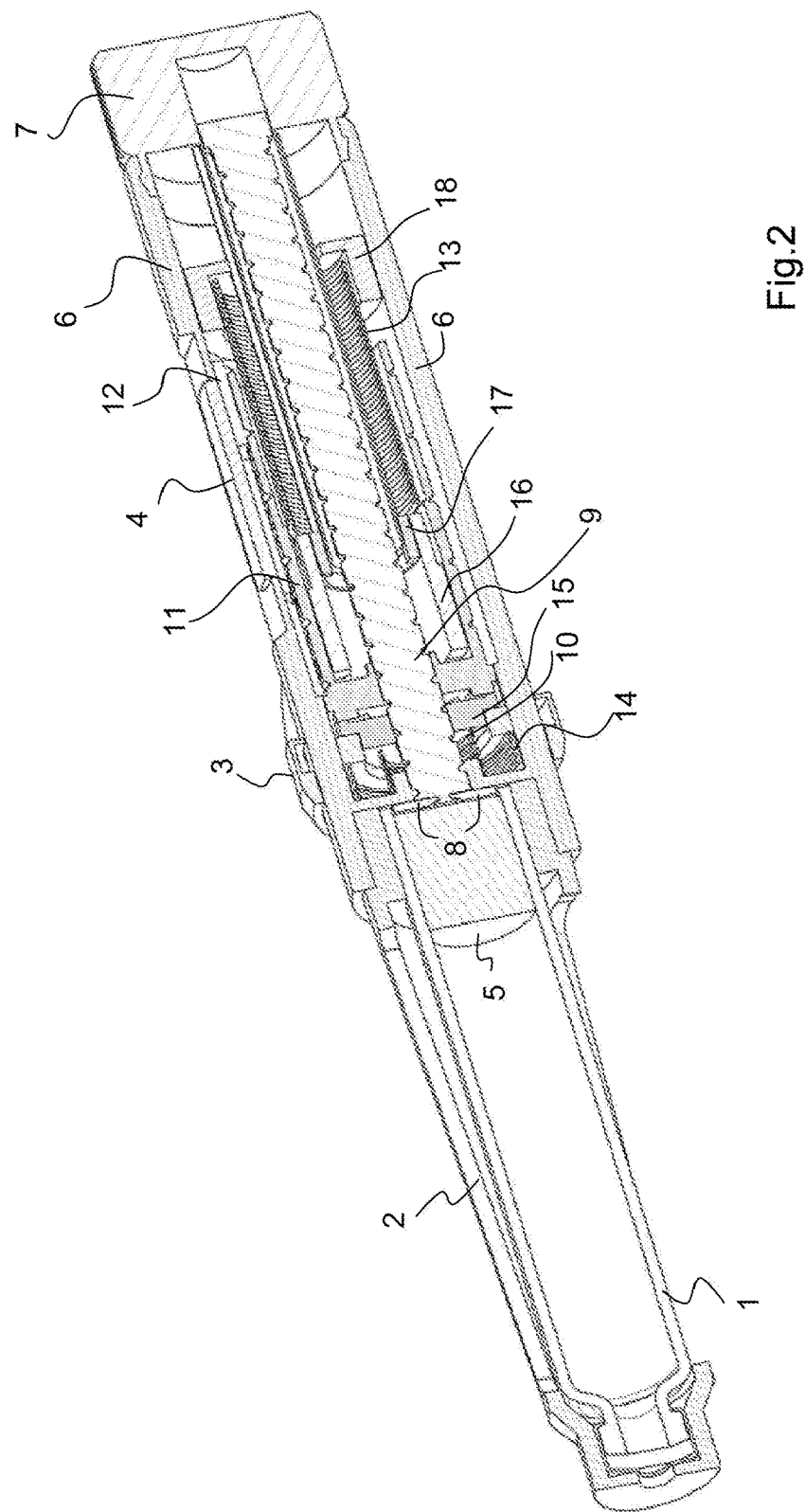
FIG. 2 shows a cross section of an embodiment of the mechanism.

FIG. 2 shows a cross section of an embodiment of the mechanism, arranged in a pen-type drug delivery device, according to the device shown in FIG. 1. Elements that correspond to elements of FIG. 1 are designated with the same reference numerals in FIG. 2. Additionally to the fixed window 4, the bung 5, the body 6 and the dial 7, FIG. 2 shows a lead screw 9 with an optional bearing 8 arranged between the bung 5 and the lead screw 9, a resilient element 10, which may be a helical spring, for instance, an indicator member in the shape of a number sleeve 11, a movable window, which may especially be a sliding window 12, and which may be provided as a part of the display, a main spring 13, a trigger spring 14, which may be a helical spring, for instance, a drive member, which may have any suitable shape like a nut, a ring or a sleeve, for instance, and will be designated as drive disc 15 in the following description, an intermediate sleeve 16 provided as a coupling element, a dial nut 17, and a spring cap 18 provided for the main spring 13. The arrangement and function of these parts will become apparent from the following detailed description.

Figure 3:
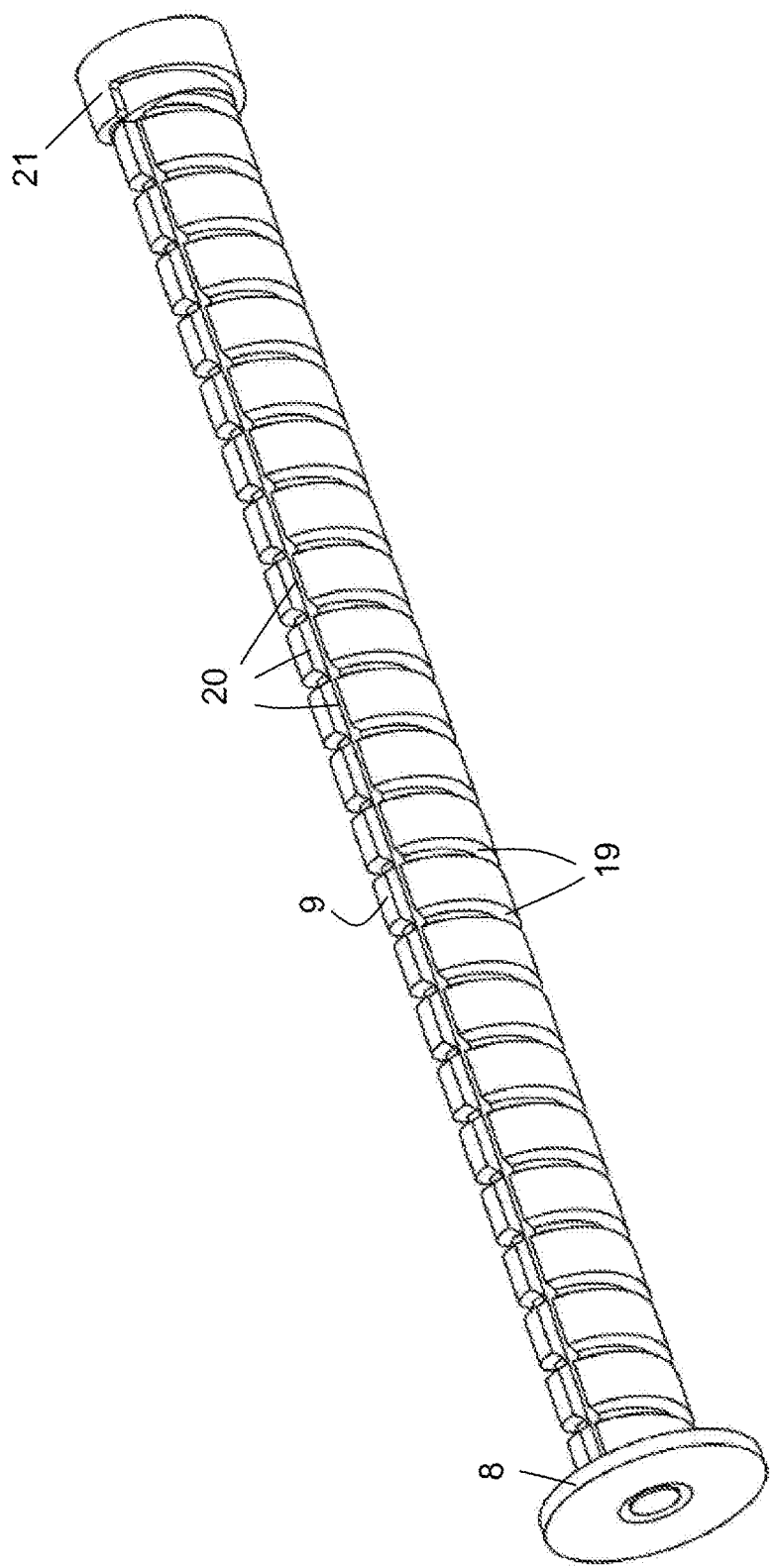
FIG. 3 shows a lead screw comprising a thread, an axial groove and a bearing.

FIG. 3 shows the lead screw 9 with the bearing 8. The distal end of the lead screw 9 connects to the bearing 8 to permit a relative rotation but prevent an axial separation of the bearing 8 and the lead screw 9. The distal face of the bearing 8 abuts the bung 5 in order to facilitate the transmission of a helical movement of the lead screw 9 to a translation of the bung 5, which expels the drug in the distal direction. The presence of a bearing 8 is preferred but it is optional. The lead screw 9 comprises a screw thread 19, which is left-handed in the example shown in FIG. 3, but may instead be right-handed. The differences deriving from the different types of the screw thread 19, which yield essentially similar mechanisms, will become apparent from the following description. The lead screw 9 is provided with a structure that allows a further element to slide axially along the lead screw 9 and rotationally locks the further element relative to the lead screw 9. This structure may comprise a plurality of splines arranged in a line and/or a groove 20, which intersects the screw thread 19 without inhibiting a threaded engagement with a further element. The described embodiment comprises a pair of straight grooves 20 arranged opposite to one another parallel to the axis of the lead screw 9. A further structure may be provided near the proximal end of the lead screw 9 to form a last-dose abutment 21 of the lead screw 9. The function of the last-dose abutment 21 will be described below.

Figure 4:
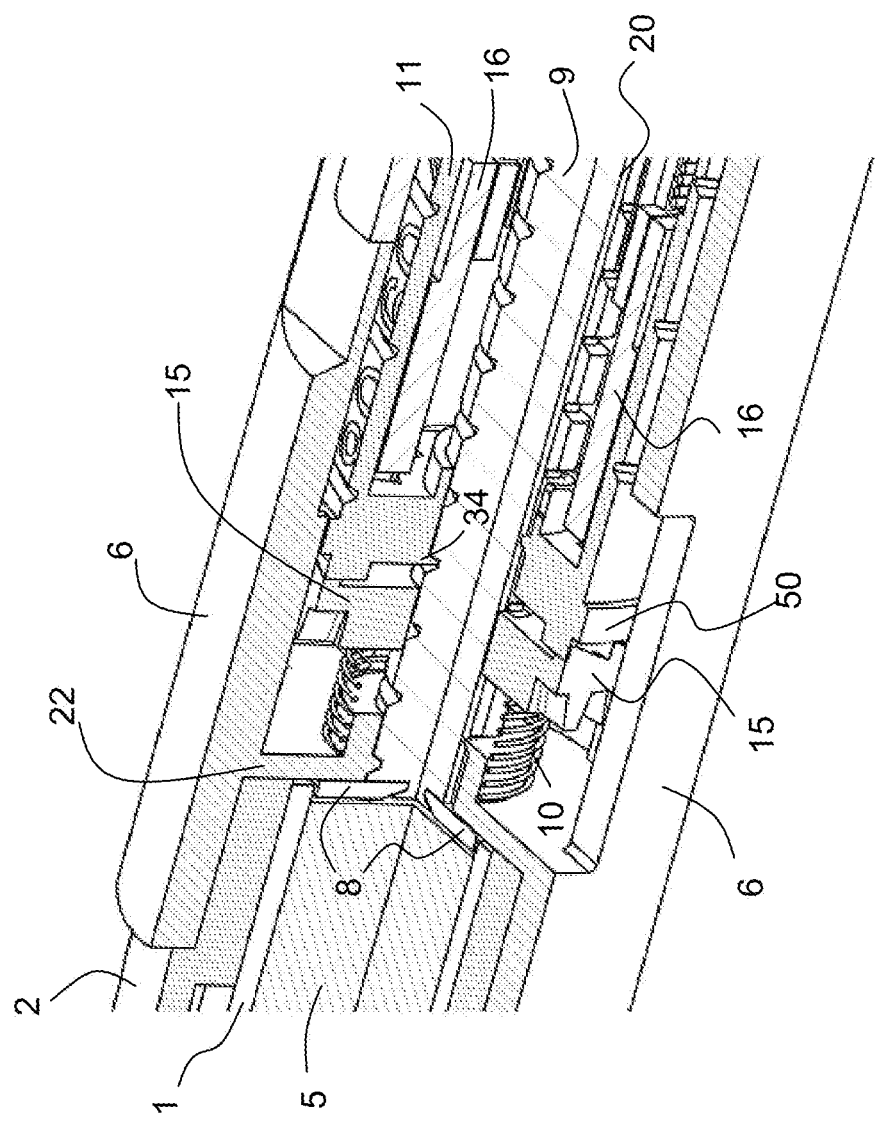
FIG. 4 is a cutaway view of a middle section of the embodiment according to FIG. 2.

FIG. 4 is a cutaway view of a middle section of the embodiment according to FIG. 2 with the trigger 3 and the trigger spring 14 removed. FIG. 4 shows how the lead screw 9 can be rotationally locked to the drive disc 15 by means of the groove 20 engaging a spline or protrusion of the drive disc 15. Splines of the lead screw 9 may instead engage grooves of the drive disc 15. The lead screw 9 and the drive disc 15 are coupled in such a manner that they are only able to rotate simultaneously, whereas an axial movement of the lead screw 9 relative to the drive disc 15 is possible. A threaded body web 22 is provided to guide a helical movement of the lead screw 9 relative to the body 6. The helical movement is left-handed if the thread 19 of the lead screw 9 is left-handed. In this case a counterclockwise rotation of the drive disc 15, viewed in the distal direction, causes the lead screw 9 to advance helically in the distal direction. If the lead screw 9 is instead provided with a right-handed thread 19, a clockwise rotation of the drive disc 15 makes the lead screw 9 advance in the distal direction. The threaded body web 22 is particularly suitable, but a threaded engagement between the body 6 and the lead screw 9 can instead be effected by another part or component of the body 6. FIG. 4 further shows a first thread 34 of the number sleeve 11, which is thereby threadedly engaged with the lead screw 9. The first thread 34 may be formed in a central bore of a distal flange 50 of the number sleeve 11, for example.

Figure 5:
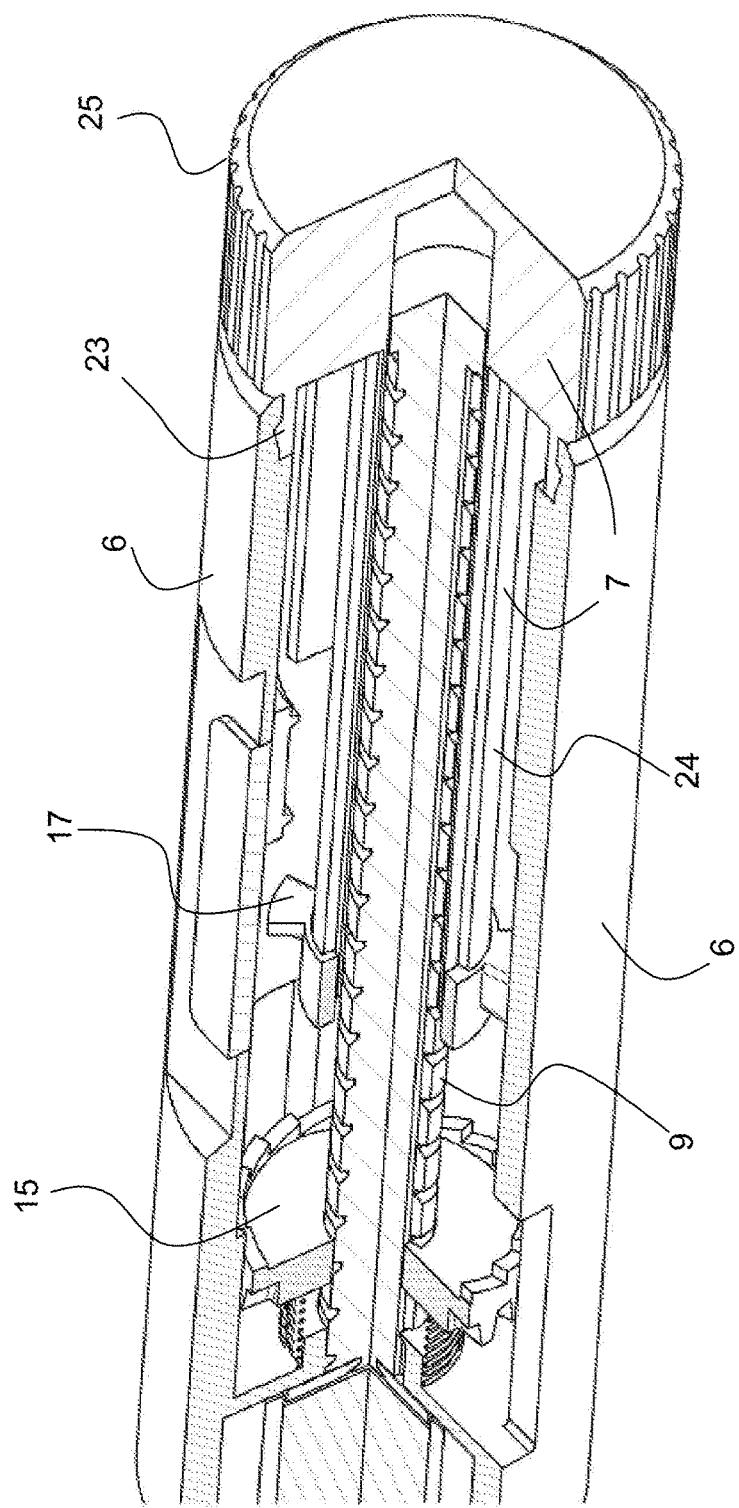
FIG. 5 is a cutaway view of a proximal section of the embodiment according to FIG. 2.

FIG. 5 is a cutaway view of a proximal section of the embodiment according to FIG. 2. The dial 7 comprises an axial constraint 23, a sleeve 24 inside the body 6 and a button 25 outside the body 6, while other shapes of the dial 7 may be suitable as well. The axial constraint 23 is provided to allow a free rotation of the dial 7 and to prevent a translation, thus axially constraining the dial 7 to the body 6. The axial constraint 23 may be formed by a cylindrical extension of the dial 7 with a beaded rim, which is inserted in a chamfer or furrow of the body 6, for example, as shown in FIG. 5. The dial 7 may thus be turned without being separated from the body 6. The rotation is transferred to the dial nut 17, which is rotationally locked, in particular splined, for example, to the sleeve 24 of the dial 7. An axial movement of the dial nut 17 is allowed within a limited range, as will be described below. The user of the device rotates the dial 7 by means of the button 25 to set and unset a dose. In the described embodiment a clockwise rotation of the dial 7 increases the dose set whereas a counterclockwise rotation decreases the dose set.

FIG. 6 shows a schematic cross section of the middle section of the described embodiment of the mechanism. FIG. 6 shows the relative positions of the lead screw 9, the number sleeve 11, the drive disc 15, the intermediate sleeve 16, and the dial nut 17, which is axially constrained in the proximal direction (to the right in the arrangement shown in FIG. 6) by abutments 26 on an inner surface of the number sleeve 11. The abutments 26 may engage with radial bosses 51 of the dial nut 17, for example. The radial bosses 51 also rotationally link the dial nut 17 to the intermediate sleeve 16 and are profiled to transfer a torque to the intermediate sleeve 16 during setting of a dose and to transfer both a torque and an axial force to the intermediate sleeve 16 during a cancellation of the dose set. The intermediate sleeve 16 thus obtains the function of a reversing sleeve.

FIG. 7 is a cutaway view of a distal part of the mechanism. The cross section face 29 is not an actual surface of the body 6 but represents an imaginary plane that is formed by the cross section only. Ratchet features, which may be ratchet teeth 27, on the distal face of the number sleeve 11 engage with corresponding features on the drive disc 15. Each of the ratchet teeth 27 has preferably two engaging surfaces, which extend essentially radially with respect to the axis of the body 6, are ramped in opposite azimuthal directions and have different slopes. When the ratchet teeth 27 are engaged, corresponding surfaces of the ratchet teeth 27 are in contact. The different slopes cause a unidirectional rotational coupling between the number sleeve 11 and the drive disc 15, which are rotationally locked in one sense of rotation, while the ratchet can be overridden in the opposite sense of rotation. In the described embodiment, the number sleeve 11 and the drive disc 15 are rotationally locked when the number sleeve 11 is rotated counterclockwise with respect to the distal direction. The resilient element 10 acts between the body 6 and the drive disc 15 and applies an axial force on the drive disc 15 in the proximal direction to maintain the engagement of the ratchet features. The resilient element 10 may be a helical spring which is supported by an inner body face 28, which may be a proximal surface of the threaded body web 22, for example.

Figure 8:
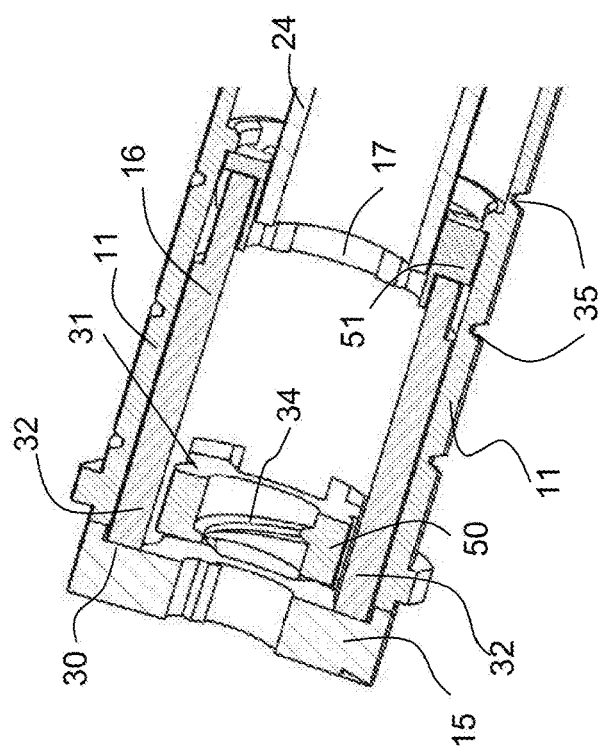
FIG. 8 is a cutaway view of coupled elements of the mechanism.

FIG. 8 is a cutaway view of coupled elements of the mechanism. The intermediate sleeve 16 is splined to the number sleeve 11. This can be achieved by a spline engagement 31 of an axial boss 32 protruding through the distal flange 50 of the number sleeve 11. The axial boss 32 abuts the drive disc 15 and is thus in a position to push the drive disc 15 axially in the distal direction. There may be any number of such axial bosses 32, of which there are four in the described embodiment. FIG. 8 also clearly shows how the first thread 34 of the number sleeve 11, which is provided for a threaded engagement with the lead screw 9, may be formed in the central bore of the distal flange 50 of the number sleeve 11.

Figure 9:
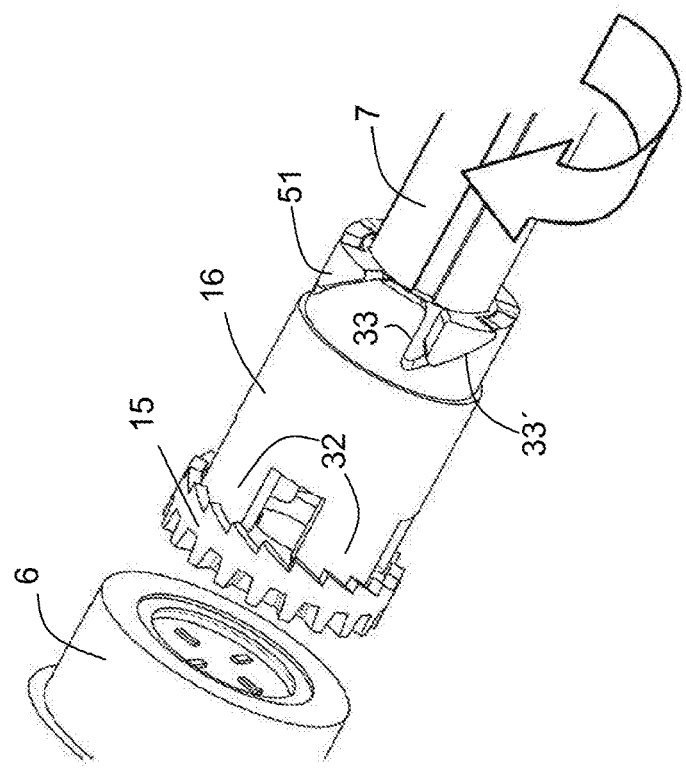
FIG. 9 is a further cutaway view of the part of the mechanism shown in FIGS. 7 and 8.

FIG. 9 is a further cutaway view of the part of the mechanism shown in FIGS. 7 and 8 with the number sleeve 11 removed, and further explains the interaction of the dial nut 17 with the intermediate sleeve 16 by means of contact faces 33, 33' of different inclinations, which form a further unidirectional rotational gear or ratchet. The curved arrow in FIG. 9 indicates the clockwise rotation of the dial 7 during dose setting. The torque is transferred from the dial 7 via the splined engagement with the dial nut 17 to the intermediate sleeve 16 by those contact surfaces 33 that have a steep slope. The number sleeve 11 is simultaneously rotated because of the splined engagement of the intermediate sleeve 16, which may be achieved with axial bosses 32 of the intermediate sleeve 16 engaging recesses of the distal flange 50 of the number sleeve 11, as described above. As the number sleeve 11 is threadedly engaged with the lead screw 9 by the first thread 34, a rotation of the number sleeve 11 generates a translation of the number sleeve 11 when the lead screw 9 is kept rotationally locked relative to the body 6, as will be described below.

Figure 10:
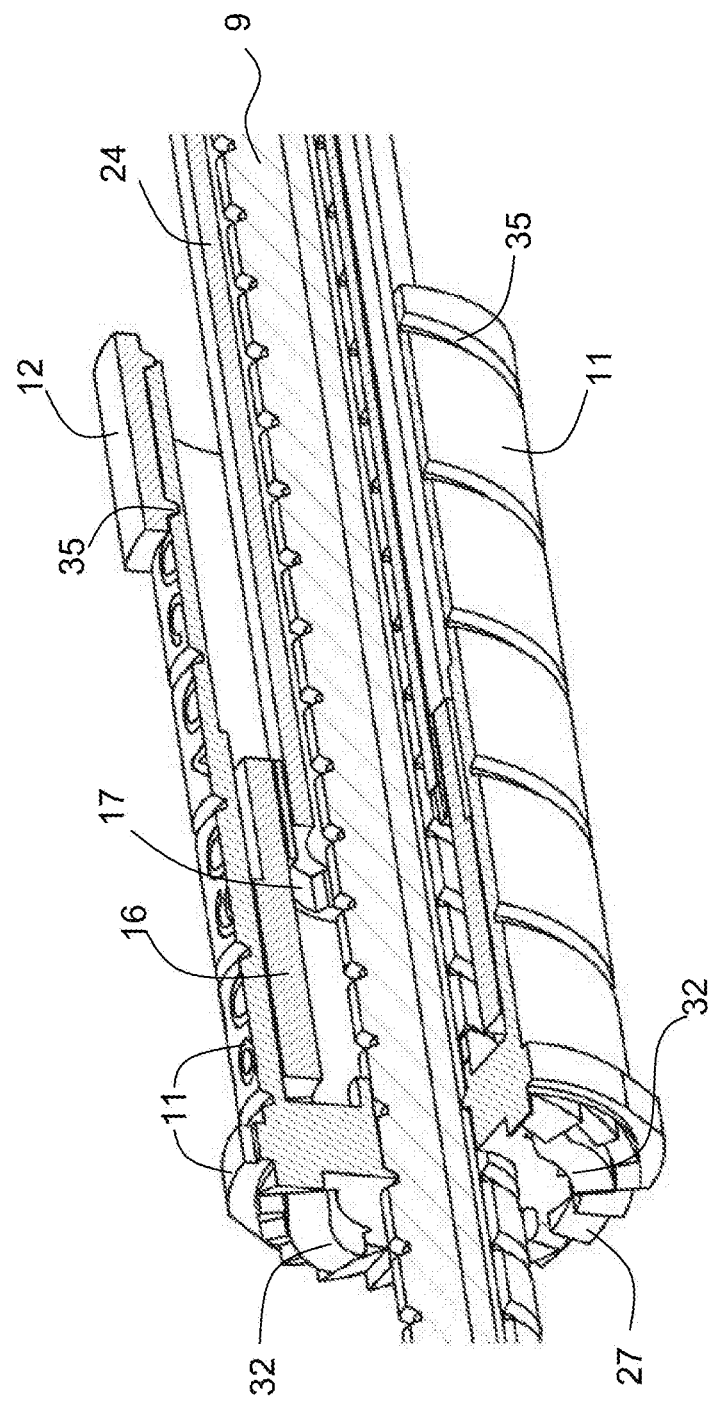
FIG. 10 is a cutaway view showing the arrangement of threads on elements of the mechanism.

FIG. 10 is a cutaway view showing the arrangement of threads on elements of the mechanism. The number sleeve 11 is threaded to the lead screw 9 by the first thread 34 and to the sliding window 12, which is a part of a window arrangement, by a second thread 35. The fixed window 4 and the sliding window 12 form the window arrangement, and the sliding window 12 is movable within dimensions of the fixed window 4. As the design of the sliding window 12 limits its movements to translations within the dimensions of the fixed window 4, a rotation of the number sleeve 11 generates an axial movement of the sliding window 12. As a result of the various engagements described above a clockwise rotation of the sleeve 24 of the dial 7 generates simultaneous clockwise rotations of the dial nut 17, the intermediate sleeve 16 and the number sleeve 11, and the left-handed first thread 34 makes the number sleeve 11 move in the proximal direction, as long as the lead screw 9 stays stationary with respect to the body 6. Accordingly a counterclockwise rotation of the sleeve 24 of the dial 7 generates simultaneous counterclockwise rotations of the dial nut 17, the intermediate sleeve 16 and the number sleeve 11, and the left-handed first thread 34 makes the number sleeve 11 move in the distal direction. The second thread 35 is also left-handed if the first thread 34 is left-handed and is right-handed if the first thread 34 is right-handed. In any case an axial movement of the number sleeve 11 in the proximal direction generates an axial movement of the sliding window 12 in the distal direction and vice versa. The range of the movement of the sliding window 12 relative to the number sleeve 11 is thus considerably larger than the distances covered by either element with respect to the body 6. This facilitates the implementation of this type of display in a compact device.

Figures 11A, 11B, 11C:
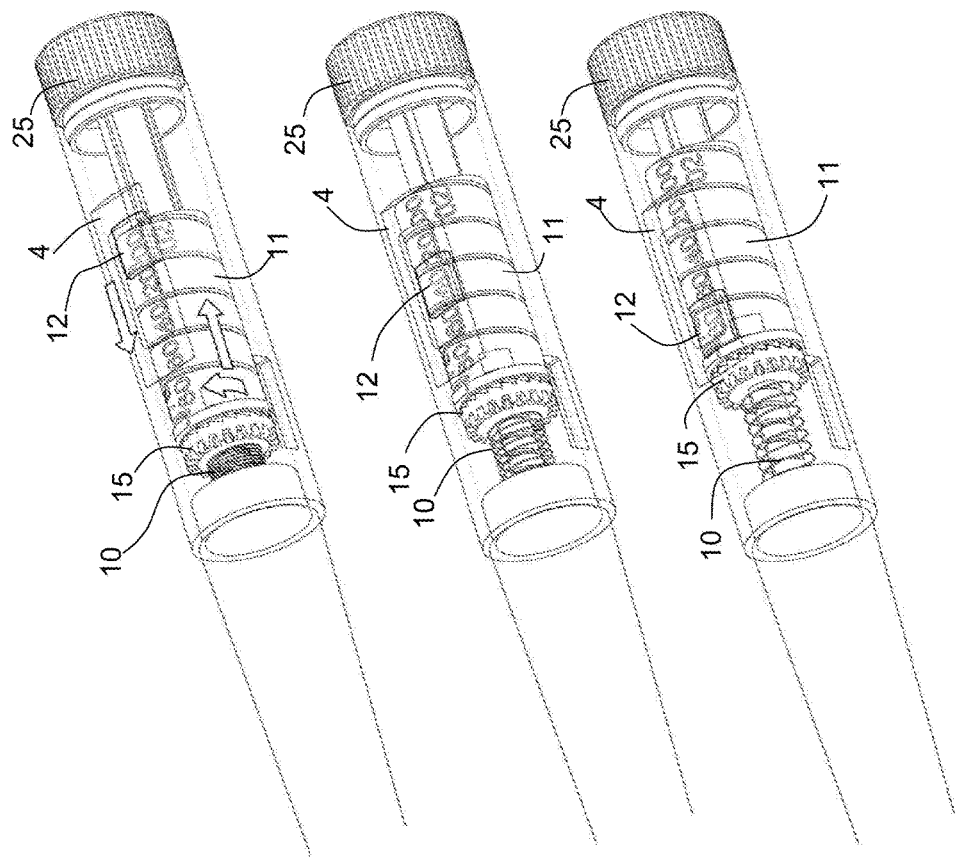
FIG. 11 shows semitransparent views of the proximal part of a drug delivery device in different states during dose dialling.

FIG. 11 shows semitransparent views of the proximal part of a drug delivery device in different states during dose dialling. FIG. 11A shows the state with no dose yet dialled and the sliding window 12 at its most proximal position. When the button 25 of the dial 7 is turned clockwise, according to the curved arrow, the sliding window 12 starts to move in the distal direction, as indicated by the upper straight arrow, and the number sleeve 11 starts to move in the proximal direction, as indicated by the lower straight arrow. FIG. 11B shows the state with the dose partially dialled and the sliding window 12 passed halfway through the fixed window 4. It can be seen that the engagement between the number sleeve 11 and the drive disc 15 is maintained by means of the resilient element 10. FIG. 11C shows the state with a maximal dose dialled and the sliding window 12 at its most distal position. The resilient element 10 is maximally extended, but the engagement between the number sleeve 11 and the drive disc 15 is still maintained.

FIG. 12 is a further cutaway view of the part of the mechanism according to FIG. 7 for the state of the mechanism in which no dose is set. An end-of-dose stop 36 may be provided by a radially extending abutment feature on the number sleeve 11. The abutment feature is provided to engage with a spline or a similar feature of the body 6 to prevent a cancelling rotation, which is counterclockwise in the described embodiment, when no dose is dialled or cancelling is completed.

The dose to be dispensed can be displayed on the number sleeve 11 through the fixed window 4 and the sliding window 12. To this end the sliding window 12 displays a surface area of the number sleeve 11, which may be provided with a helical path of numbers 38, the pitch of the helix matching the pitch of the second thread 35 of the number sleeve 11 coupling the number sleeve 11 and the sliding window 12. The path of numbers may be printed directly on the number sleeve 11, for instance, or it may be provided by a printed sheet or foil, which is wrapped around the number sleeve 11.

FIG. 13 is a further cutaway view of the part of the mechanism according to FIG. 7 for the state of the mechanism in which a maximal dose is set. A maximum-dose stop 37 may be provided by a further radially extending abutment feature on the number sleeve 11. When a maximal dose has been dialled, the further abutment feature stops the rotation of the number sleeve 11 by abutting the sliding window 12, which approaches the distal end of the fixed window 4 in this state of dialling.

The number 38 on the number sleeve 11 indicating the dose set is preferably displayed through the sliding window 12. Even if the fixed window 4 stays open in its entirety, the display can be confined to the area of the sliding window 12. This may be achieved by using a transparent cover of the fixed window 4 that is profiled to distort the light path sufficiently to make the numbers on the number sleeve 11 illegible when viewed through the fixed window 4 alone. The sliding window 12 is designed to correct the optical distortion caused by the fixed window 4 to ensure that the number 38 corresponding to the dose set is legible, while the other numbers, which are not in the area of the sliding window 12, remain illegible. The sliding window 12 may alternatively or additionally provide a magnifying effect to increase the character size of the display.

FIG. 14 shows an example of such a display of the drug delivery device. The arrangement of the display including the fixed window 4 and the sliding window 12 is shown in FIG. 14A. The numbers of the number sleeve 11 are visible in the open fixed window 4, but only the number in the bordered frame of the sliding window 12 is easily legible. This is achieved by a distorting surface structure of the transparent cover of the fixed window 4 that is optically compensated by the sliding window 12, which is preferably provided with the complementary surface structure. FIG. 14B shows an embodiment in which the surface structure forms a waved surface comprising a plurality of parallel ridges 39, for instance, with curved valleys in between. The surface of the sliding window 12 that faces the structured surface of the fixed window 4 is provided with corresponding ridges, which are arranged between the ridges 39 of the fixed window 4 and form a complementary waved surface. The ridges 39 are arranged in the axial direction to allow the sliding window 12 to move over the fixed window 4 with the corresponding waved surfaces touching one another. The number and form of the ridges 39 are adapted to obtain the desired optical effect. FIG. 14C shows a further embodiment of a transparent cover of the fixed window 4 in a cross section transverse to the axial direction. In this example the ridges 39 are smoothly curved while the valleys in between are not. The complementary surface of the sliding window 12 comprises smoothly curved grooves between sharp ridges. The curved ridges may instead be formed on the sliding window 12 and the corresponding grooves and sharp ridges on the transparent cover of the fixed window 4. The examples show that any optically distorting shape of the surface structure may be suitable that allows the sliding window 12 to move axially relative to the fixed window 4.

FIG. 15 shows a further example of the display. In this embodiment the transparent cover of the fixed window 4 forms a distorting lens 40 having a V-shaped cross section transverse to the axial direction. The distorting lens 40 distorts the numbers outside the area of the sliding window 12, which has a complementary shape in order to compensate the optical effect of the V-shaped distorting lens 40. Therefore the number behind the sliding window 12 is not distorted. FIG. 15C shows a further embodiment of a transparent cover of the fixed window 4 having a triple V-shaped distorting lens 40 in a cross section transverse to the axial direction. The examples show that any optically distorting lens 40 may be suitable that allows the sliding window 12 to move axially relative to the fixed window 4.

FIG. 16 shows still a further example of the display. In this embodiment the transparent cover of the fixed window 4 forms a magnifying lens 41, which magnifies the numbers outside the area of the sliding window 12 in the vertical direction. In order to compensate the optical effect of the magnifying lens 41 and to bring the number to be read back into focus, the sliding window 12 has a complementary shape, so that the number behind the sliding window 12 is not magnified and hence not distorted. FIG. 16C shows a further embodiment of a transparent cover of the fixed window 4 having a magnifying lens 41 in a cross section transverse to the axial direction. The examples show that any optically distorting magnifying lens 41 may be suitable that allows the sliding window 12 to move axially relative to the fixed window 4.

Figure 17:
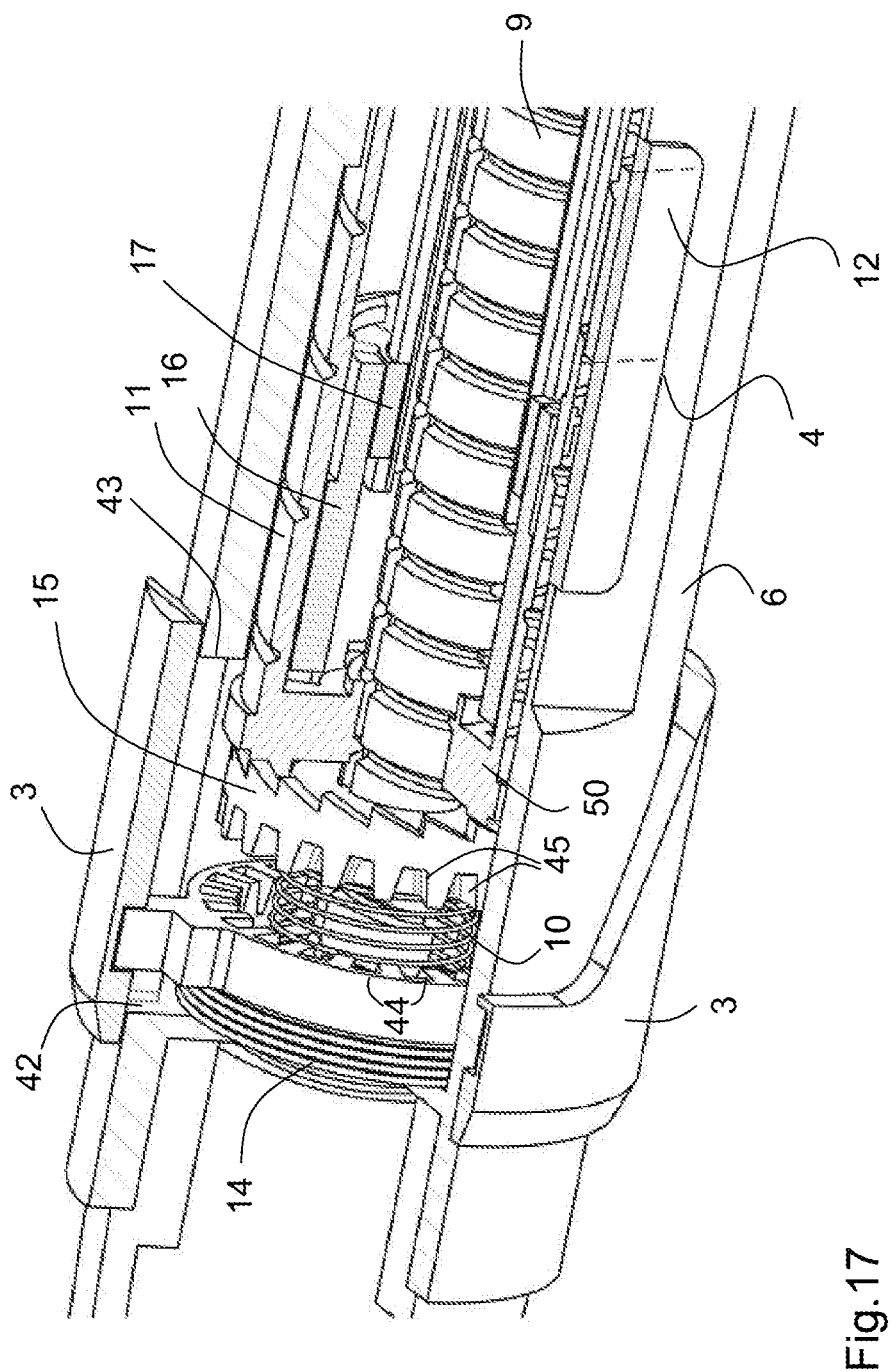
FIG. 17 is a further cutaway view of the middle section of the embodiment according to FIG. 4 including additional details.

FIG. 17 is a further cutaway view of the middle section of the embodiment according to FIG. 4 including additional details. The trigger 3 is rotationally locked to the body 6 and is free to translate axially between a distal stop feature 42 and a proximal stop feature 43. As long as the trigger mechanism is not operated by a user, splines 44 of the trigger 3 engage with corresponding splines 45 of the drive disc 15, thus preventing a rotation of the drive disc 15 and the lead screw 9, which is rotationally locked with the drive disc 15. The splines 44, 45 thus form a locking feature releasably, especially rotationally, locking the drive disc 15 to the trigger 3, the locking being released for drug delivery, as will be described below. The trigger spring 14 acts between the body 6 and the trigger 3 and applies an axial force in the proximal direction to the distal face of the trigger 3 to maintain the engagement with the drive disc 15. In the state shown in FIG. 17 the trigger 3 has been moved distally, the trigger spring 14 is compressed, and the splines 44, 45 are not engaged.

FIG. 18 is a semitransparent view of a proximal section of an embodiment of the mechanism. The main spring 13 is a torsion spring, which can be loaded by a rotation of the number sleeve 11. The ends of the main spring 13 are fixed to the number sleeve 11 and to a spring cap 18, respectively. The distal fastening 46 of the main spring 13 to the number sleeve 11 and the proximal fastening 47 of the main spring 13 to the spring cap 18 are shown in FIG. 18. The spring cap 18 is rotationally locked to the body 6 but is preferably free to move axially with the main spring 13. This may be achieved by grooves or splines 48 that are arranged in the axial direction. The free translation of the spring cap 18 is preferred because it allows the axial extension of the main spring 13 to be essentially maintained, thus avoiding an additional strain that would be caused by a compression of the main spring 13 during the intended torsional charging. Furthermore, the effective torque is larger when the loaded main spring 13 is released without being extended. This will become clear from the following description of the dose setting and delivery operations.

FIG. 18 also shows the sliding window 12, which is engaged with the number sleeve 11 by the second thread 35 of the number sleeve 11. The main spring 13 is preferably pre-wound upon assembly, such that it applies a torque to the number sleeve 11 when the mechanism is in the end-of-dose state. A rotation of the dial 7 to set a dose also rotates the dial nut 17, the intermediate sleeve 16 and the number sleeve 11, relative to the body 6 and the spring cap 18, and winds up the main spring 13. The torque applied to the main spring 13 is reacted at the proximal end by the body 6 via the spring cap 18. At the distal end the torque is reacted by the trigger 3, via the ratchet feature, especially ratchet teeth 27, between the number sleeve 11 and the drive disc 15 and the splines 44, 45 coupling the drive disc 15 to the trigger 3.

The setting of a dose will now be explained in conjunction with FIGS. 19 to 22. FIG. 19 is a semitransparent view of the proximal section of the embodiment according to FIG. 11, including details from FIGS. 17 and 18, and FIG. 20 is a corresponding cross section. FIGS. 19 and 20 show the initial state of the drug delivery device as delivered, ready to set the first dose, with the end-of-dose stop 36 still engaged. To set a dose, the dial 7 is rotated clockwise by means of the button 25, so that the number sleeve 11 is simultaneously rotated by means of further parts of the mechanism described above, as shown in the cross section of FIG. 20. The number sleeve 11 translates in the proximal direction because of its threaded engagement with the lead screw 9, which remains stationary. As the number sleeve 11 rotates, the second thread 35 causes the sliding window 12 to move across the helical path of numbers 38 in the distal direction, so that the number 38 that is visible behind the sliding window 12 changes corresponding to the dose set. The ratchet teeth 27 at the distal end of the number sleeve 11 ramp over the corresponding features on the drive disc 15, creating tactile and audible feedback to the user for each unit set. The ratchet features between the number sleeve 11 and the drive disc 15 prevent the main spring 13 from unwinding the number sleeve 11 when the dial 7 is released.

Both the drive disc 15 and the trigger 3 match the axial translation of the number sleeve 11 owing to the resilient element 10 and the trigger spring 14, which maintain the engagement of the ratchet teeth 27 between the drive disc 15 and the number sleeve 11 and the engagement of the splines 44, 45 coupling the drive disc 15 and the trigger 3. The trigger spring 14 acts on the trigger 3 in such a way that the trigger spring 14 tends to keep the drive disc 15 locked to the trigger 3. The trigger 3 is moved from a start position to an end position relative to the body 6 during the setting of a dose, the end position having a distance from the start position that increases as the dose set increases. The end position of the trigger 3 may especially have a distance from the start position that is proportional to the dose set. As the dial 7 is rotated relative to the body 6 the main spring 13 is charged in torsion. The spring cap 18 translates with the number sleeve 11, via the main spring 13, in order to allow the main spring 13 to match the axial translation of the number sleeve 11.

FIG. 21 is a semitransparent view according to FIG. 19 for the state of the mechanism, in which the maximal dose is dialled and the maximum-dose stop 37 is engaged, and FIG. 22 is a corresponding cross section. The user may continue to dial up until the maximum-dose stop 37 is reached. During the dialling operation the trigger 3 and the drive disc 15 translate axially, so that the splines 44 of the trigger 3 remain engaged with the splines 45 of the drive disc 15 until the dialling is stopped. The spring cap 18 is translated towards its proximal position to prevent an overload of the main spring 13. When nearly all the doses available in the drug delivery device have been delivered and the final dose is dialled, the rotation of the dial 7 is stopped when the last-dose abutment 21 of the lead screw 9 engages the number sleeve 11, which may occur before the maximum-dose stop 37 is reached, as will be described below.

FIGS. 23 and 24 are further cutaway views of the middle section of the embodiment of the mechanism including details from FIGS. 4 and 17, the trigger 3 being omitted for clarity. FIGS. 23 and 24 explain the operation of a last-dose feature. FIG. 23 shows the mechanism after a number of doses have been delivered, with the device in the end-of-dose state. The last-dose abutment 21 of the lead screw 9 is still at a distance from a corresponding last-dose abutment 49 of the number sleeve 11. FIG. 24 shows a later state of the mechanism, when a dose has been dialled causing the number sleeve 11 to move helically towards the proximal end of the device, when the last-dose abutment 21 of the lead screw 9 is in contact with the last-dose abutment 49 of the number sleeve 11. Further dialling up of the mechanism is therefore prevented, as the lead screw 9 is rotationally locked, and contact of the last-dose abutment 21, 49 rotationally locks the number sleeve 11 in the clockwise direction.

Figure 25A:
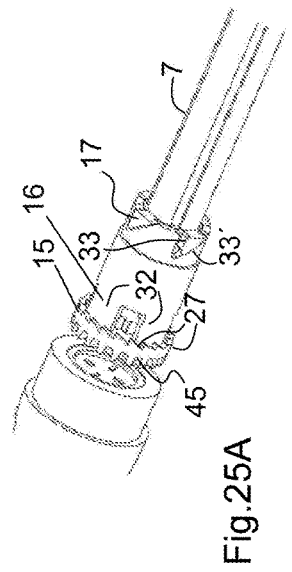
FIG. 25 shows further cutaway views according to FIG. 9 for a state of the mechanism at the start of a cancellation of the dose set.
Figure 25B:
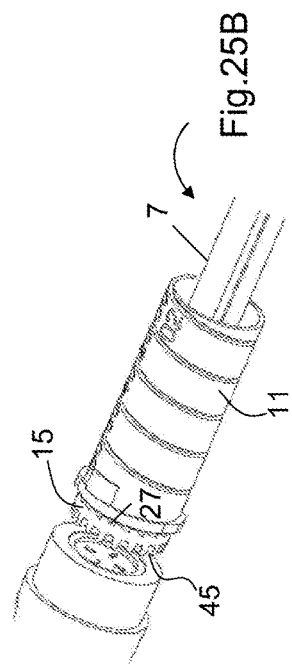
Figure 26A:
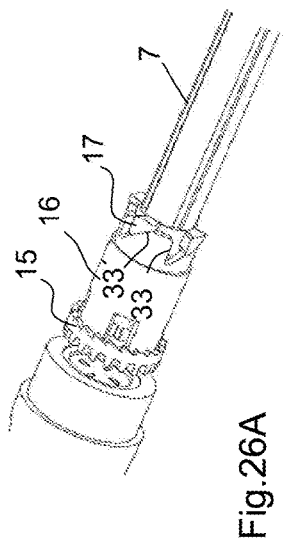
FIG. 26 shows further cutaway views according to FIG. 25 for a state of the mechanism during the cancellation of the dose set.
Figure 26B:
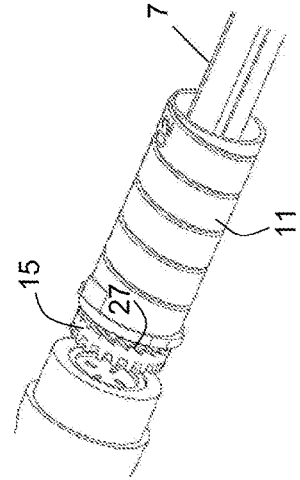
Figure 27A:
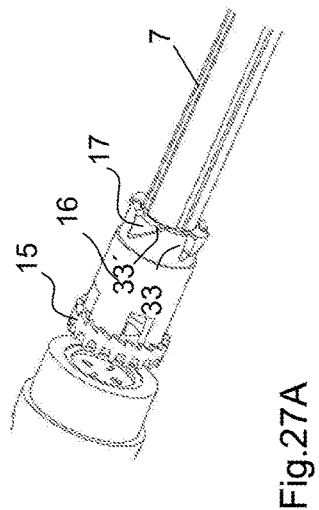
FIG. 27 shows further cutaway views according to FIG. 25 for a state of the mechanism at the end of a step for cancelling the dose set.
Figure 27B:
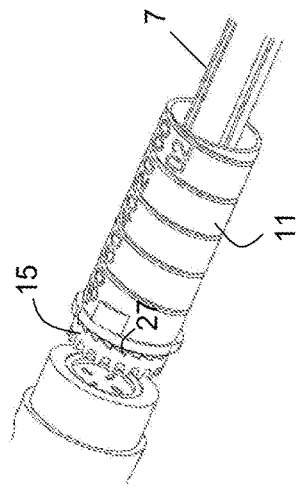

The cancellation of a set dose will now be described in conjunction with FIGS. 25 to 27, which show further cutaway views according to FIG. 9 for different states of the mechanism during a dose cancelling operation. A set dose can be cancelled by a rotation of the dial 7 in the opposite sense of the rotation during setting. In the described embodiment, the cancellation of a set dose involves a counterclockwise rotation of the dial 7, which rotates the dial nut 17 relative to the intermediate sleeve 16, which is rotationally locked to the body 6, because the intermediate sleeve 16 is rotationally locked to the number sleeve 11 by the spline engagement 31, the number sleeve 11 is unidirectionally rotationally locked to the drive disc 15 by the ratchet teeth 27, and the drive disc 15 is rotationally locked to the body 6 via the trigger 3. FIG. 25A shows the positions of the drive disc 15, the intermediate sleeve 16 and the dial nut 17, and FIG. 25B shows the arrangement of the drive disc 15 and the number sleeve 11 during the counterclockwise rotation of the dial 7, indicated by the curved arrow. FIG. 26A shows how the dial nut 17 overrides the ramped contact faces 33' of the unidirectional rotational gear by pushing the intermediate sleeve 16 in the distal direction; the dial nut 17 is axially constrained in the proximal direction by the abutments 26 of the number sleeve 11, as explained above in conjunction with FIG. 6. The axial bosses 32 of the intermediate sleeve 16 push the drive disc 15 out of its engagement with the number sleeve 11, and the number sleeve 11 is free to rotate counterclockwise, as shown in FIG. 26B. The rotation of the number sleeve 11 is accelerated by the torque of the loaded main spring 13. This causes the intermediate sleeve 16, which is rotationally locked to the number sleeve 11 by the spline engagement 31, to rotate counterclockwise relative to the dial 7 and the dial nut 17, sliding helically over the ramped contact faces 33'. This results in an axial movement of the intermediate sleeve 16 back in the proximal direction, as shown in FIG. 27A, until the steep contact faces 33 are again in contact, and the ratchet features of the number sleeve 11 and drive disc 15 are again engaged, as shown in FIG. 27B, by means of the resilient element 10. The number sleeve 11 is now again prevented from rotating counterclockwise. As long as the dial 7 is rotated counterclockwise by the user, the described process is repeated until the end-of-dose condition is reached and the end-of-dose stop 36 engages.

The dose delivery will now be described in conjunction with FIGS. 28 to 33. FIG. 28 is a semitransparent view of the mechanism at the start of dispense, when the maximal dose is dialled and the sliding window 12 displays the maximal number of units, which is 80 in this example. The main spring 13 is loaded and the spring cap 18 is in its proximal position near the button 25 of the dial 7. The arrangement of the trigger 3, the drive disc 15, the number sleeve 11, the intermediate sleeve 16, the main spring 13, the spring cap 18 and the lead screw 9 is shown in FIG. 29. The trigger spring 14 is extended, but maintains the coupling between the trigger 3 and the drive disc 15 by means of the splines 44, 45.

The dose set is dispensed by translating the trigger 3 in the distal direction with respect to the body 6, compressing the trigger spring 14, as shown in FIG. 28. This releases the splined engagement between the trigger 3 and the drive disc 15, allowing the drive disc 15 to rotate, driven by the number sleeve 11, which is rotated by the loaded main spring 13. The cross section of FIG. 29 shows how the rotating drive disc 15 turns the lead screw 9 counterclockwise, because the drive disc 15 is rotationally locked to the lead screw 9 by grooves or splines 20 shown in FIG. 4. As the left-handed thread 19 of the lead screw 9 is guided by a thread of the body 6, especially by the threaded body web 22 shown in FIG. 4, for instance, the lead screw 9 advances helically in the distal direction and drives the bung 5, so that the dose set is expelled from the receptacle, especially from the medicament cartridge 1, for instance. The spring cap 18 translates in the distal direction, so that the main spring 13 is not extended, which would counteract the release of the charged torsion.

Since the main spring 13 also acts on the number sleeve 11, the number sleeve 11 rotates counterclockwise at the same rate as the drive disc 15. The ratchet between the number sleeve 11 and the drive disc 15 remains in engagement as these two parts translate with the lead screw 9, maintaining the transmission of torque from the main spring 13. During the counterclockwise rotation of the number sleeve 11, the sliding window 12 is moving in the proximal direction and thereby displays a sequence of numbers 38 indicating a decreasing amount of the dose remaining to be dispensed. The rotational locks that are provided in the mechanism cause the intermediate sleeve 16, the dial nut 17 and the dial 7 to rotate counterclockwise together with the number sleeve 11 during drug delivery.

Figure 30:
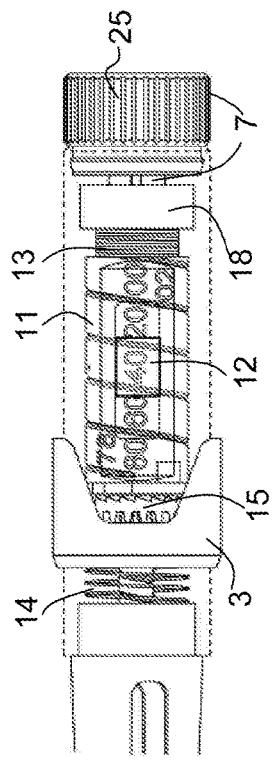
FIG. 30 is a semitransparent view according to FIG. 28 for a state of the mechanism after dispensing half of the dose set.
Figure 31:
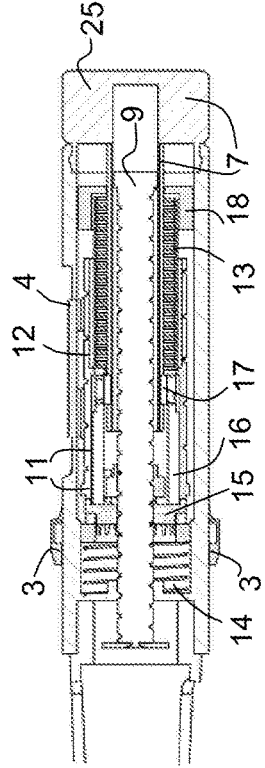
FIG. 31 is a cross section according to FIG. 29 for the state of the mechanism according to FIG. 30.

FIG. 30 shows a semitransparent view of the mechanism according to FIG. 28 for an intermediate state of the mechanism when about half the dose has been dispensed. FIG. 31 shows a corresponding cross section according to FIG. 29. The sliding window 12 has moved halfway in the proximal direction and displays 40 units remaining to be dispensed. The lead screw 9 has moved in the distal direction, and the distance between the spring cap 18 and the button 25 has increased. Since the drive disc 15 progressively translates during dispense, the user must continue to shift the trigger 3 to the distal end by further compressing the trigger spring 14, in order to keep the trigger 3 disengaged from the drive disc 15. This provides clear tactile feedback that the dose is being dispensed, while still requiring a low user force regardless of the force required to move the bung 5. Releasing the trigger 3 at any time during dispense allows the trigger spring 14 to bias the splines 44 of the trigger 3 into engagement with the corresponding splines 45 of the drive disc 15, preventing a further rotation of the drive disc 15, the number sleeve 11 and the lead screw 9, and ceasing dispense. The rotation of the drive disc 15 by the main spring 13 continues until the number sleeve 11 contacts the end-of-dose stop 36 or the user releases the trigger 3. The trigger 3 is moved from the end position towards the start position during the delivery of a dose, and the distance covered by the trigger 3 during the delivery of a dose increases as the amount of drug which still has to be delivered to deliver the whole dose set decreases. The distance covered by the trigger 3 during a delivery of a dose may especially be proportional to the dose delivered.

Figure 32:
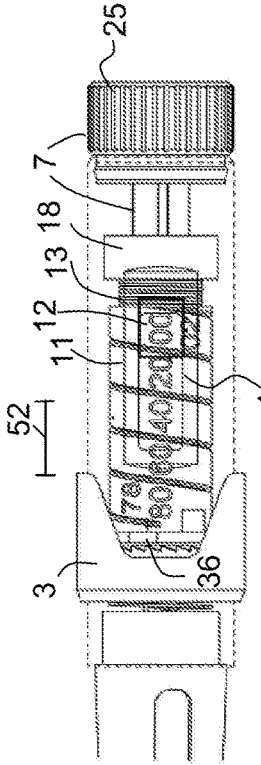
FIG. 32 is a semitransparent view according to FIG. 28 for a state of the mechanism after dose dispense.
Figure 33:
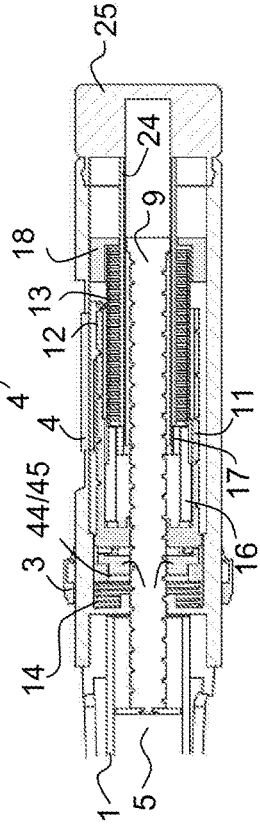
FIG. 33 is a cross section according to FIG. 29 for the state of the mechanism according to FIG. 32.

The dose delivery is completed when the end-of-dose stop 36 is reached and the mechanism is in the state shown in FIGS. 32 and 33. The movement of the trigger 3 covers an axial distance 52, which is larger the larger the dose delivered and may particularly be proportional to the dose delivered, if the threaded engagements are designed accordingly. A proportionality between the axial distance 52 and the dose delivered can be obtained by making the pitch of the thread 19 of the lead screw 9 and the pitch of the first thread 34 of the number sleeve 11 both constant, for example. The sliding window 12 is at its proximal position and displays zero units remaining to be dispensed. The spring cap 18 is at its distal position, farthest away from the button 25, and the trigger spring 14 is compressed. The lead screw 9 is in a translated position corresponding to the translated position of the bung 5. Another dose can now be set and delivered by the same operation as described above, except for the initial state according to FIGS. 19 and 20 being substituted by the state of the mechanism according to FIGS. 32 and 33.

The mechanism can be used in any drug delivery device that is operated to deliver a medicament from a receptacle like a cartridge, for instance, in a number of doses that can be selected by a user. The device is disposable and is not intended to be refilled. It is preferably delivered to the user in a fully assembled condition ready for use. The drug delivery device can be a pen-type device, for example, particularly a pen-type injector, which uses a needle to administer the dose that is dispensed.

The main spring 13 serves to store energy, which is charged as the user dials a dose and remains stored until the device is triggered for dispense by a shift of the trigger 3. Any dose size can be selected to suit individual requirements, and the dialled number of predefined units can be displayed. The mechanism permits cancelling of a dose without any medicament being dispensed by just reversing the dialling operation. The torque and force required to set and dispense a dose are independent of the force required to move the bung within the receptacle. The force required to actuate the trigger 3 is small, providing a significant ergonomic advantage, particularly for users with impaired dexterity. The mechanism can be designed in such a fashion that the trigger 3 moves by an axial distance 52 that is proportional to the volume of medicament dispensed. Very clear tactile and visual feedback may be provided to the user regarding the progress of dose delivery and thus allow them to control the delivery very precisely. Furthermore the mechanism has relatively low part count and is consequently particularly attractive for cost sensitive device applications.

The invention claimed is:

1. A dose indicating mechanism for a drug delivery device, the dose indicating mechanism comprising
   a body defining an axial direction;
   a dial that is movable relative to the body for setting a dose;
   an indicator member coupled with the dial;
   a movable window displaying a surface area of the indicator member; and
   a window arrangement comprising the movable window that is coupled to the indicator member,
   wherein the indicator member is axially movable relative to the body,
   wherein a fixed window in the body and the movable window form the window arrangement, the movable window being axially movable within dimensions of the fixed window to display the surface area of the indicator member, and
   wherein the fixed window comprises features for optical distortion, and the movable window provides a correction of the optical distortion.

2. The dose indicating mechanism according to claim 1, wherein the features for the optical distortion comprise a plurality of parallel ridges, a surface of the movable window that faces the fixed window being provided with ridges correcting the optical distortion, and the ridges are arranged in the axial direction, allowing the movable window to move with respect to the fixed window.

3. The dose indicating mechanism according to claim 1, wherein the features for the optical distortion comprise a distorting lens, and the movable window has a shape correcting the optical distortion.

4. The dose indicating mechanism according to claim 3, wherein the distorting lens has a V-shaped cross section transverse to the axial direction.

5. The dose indicating mechanism according to claim 1, wherein the features for the optical distortion comprise a magnifying lens, and the movable window has a shape compensating an optical effect of the magnifying lens.

6. The dose indicating mechanism according to claim 1, wherein the movable window is threadedly engaged with the indicator member.

7. The dose indicating mechanism according to claim 6, further comprising a helical path of numbers on the indicator member, the helical path of numbers having a pitch that matches the pitch of the thread coupling the indicator member and the movable window.

8. The dose indicating mechanism according to claim 1, wherein an axial movement of the indicator member generates an axial movement of the movable window in the opposite axial direction relative to the indicator member.

9. The dose indicating mechanism according to claim 1, wherein an axial movement of the indicator member generates an axial movement of the movable window in the opposite axial direction relative to the body.

10. A drug delivery device comprising:
    a body defining an axial direction;
    a cartridge containing a medicament;
    a dial that is movable relative to the body for setting a dose;
    an indicator member coupled with the dial;
    a movable window displaying a surface area of the indicator member; and
    a window arrangement comprising the movable window that is coupled to the indicator member,
    wherein the indicator member is axially movable relative to the body,
    wherein a fixed window in the body and the movable window form the window arrangement, the movable window being axially movable within dimensions of the fixed window to display the surface area of the indicator member, and
    wherein the fixed window comprises features for optical distortion, and the movable window provides a correction of the optical distortion.

11. The drug delivery device of claim 10, wherein the drug delivery device is a pen device.

12. The drug delivery device of claim 10, wherein the drug delivery device is a disposable device.

13. The drug delivery device of claim 10, wherein the medicament comprises at least one pharmaceutically active compound.

14. A method of operating a drug delivery device, the method comprising:
    rotating a dial to set a dose and to generate an axial movement of an indicator member such that a movable window displays a selected indication from a plurality of indications on the indicator member, the selected indication being indicative of an amount of the dose; and
    dispensing the dose,
    wherein rotating the dial causes the movable window to move within dimensions of a fixed window that optically distorts the indications on the indicator member such that the movable window is positioned to correct the optical distortion of the selected indication on the indicator member.

15. The method of claim 14, wherein rotating the dial causes the indicator member to move in a first axial direction and the movable window to move in a second axial direction opposite the first axial direction.

16. The method of claim 14, wherein rotating the dial causes the movable window to selectively magnify the selected indication.

17. A dose indicating mechanism for a drug delivery device, the dose indicating mechanism comprising:
- a body defining an axial direction;
- a dial that is movable relative to the body for setting a dose;
- an indicator member coupled with the dial;
- a movable window displaying a surface area of the indicator member, and
- a window arrangement comprising the movable window that is coupled to the indicator member, wherein the indicator member is axially movable relative to the body, and wherein an axial movement of the indicator member generates an axial movement of the movable window in the opposite axial direction relative to the indicator member.

18. A dose indicating mechanism for a drug delivery device, the dose indicating mechanism comprising:
- a body defining an axial direction;
- a dial that is movable relative to the body for setting a dose;
- an indicator member coupled with the dial;
- a movable window displaying a surface area of the indicator member, and
- a window arrangement comprising the movable window that is coupled to the indicator member, wherein the indicator member is axially movable relative to the body, and wherein an axial movement of the indicator member generates an axial movement of the movable window in the opposite axial direction relative to the body.

* * * * *